(12) United States Patent
Ago et al.

(10) Patent No.: US 11,490,974 B2
(45) Date of Patent: Nov. 8, 2022

(54) METHOD OF FIXING SURGICAL INSTRUMENT TO ROBOT ARM

(71) Applicant: MEDICAROID CORPORATION, Kobe (JP)

(72) Inventors: Kenji Ago, Kobe (JP); Kaoru Takahashi, Kobe (JP); Yu Usuki, Kobe (JP); Shota Betsugi, Kobe (JP); Tomoaki Noda, Kobe (JP); Yoshiaki Tanaka, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 483 days.

(21) Appl. No.: 16/831,843

(22) Filed: Mar. 27, 2020

(65) Prior Publication Data

US 2020/0305991 A1 Oct. 1, 2020

(30) Foreign Application Priority Data

Mar. 28, 2019 (JP) .............................. JP2019-062803
Oct. 11, 2019 (JP) .............................. JP2019-187356

(51) Int. Cl.
*A61B 34/30* (2016.01)
*A61B 90/50* (2016.01)
*A61B 34/20* (2016.01)
*A61B 34/37* (2016.01)
*A61B 46/10* (2016.01)
*A61B 17/00* (2006.01)

(52) U.S. Cl.
CPC .............. *A61B 34/30* (2016.02); *A61B 90/50* (2016.02); *A61B 34/37* (2016.02); *A61B 46/10* (2016.02); *A61B 2017/00199* (2013.01); *A61B 2017/00221* (2013.01); *A61B 2017/00398* (2013.01); *A61B 2017/00486* (2013.01); *A61B 2017/00973* (2013.01); *A61B 2034/2059* (2016.02); *A61B 2034/301* (2016.02)

(58) Field of Classification Search
CPC combination set(s) only.
See application file for complete search history.

(56) References Cited

U.S. PATENT DOCUMENTS

| 2006/0161138 | A1 | 7/2006 | Orban, III et al. |
| 2006/0235436 | A1 | 10/2006 | Anderson et al. |
| 2010/0174293 | A1 | 7/2010 | Orban, III et al. |
| 2012/0247489 | A1 | 10/2012 | Orban, III et al. |

FOREIGN PATENT DOCUMENTS

| EP | 1897511 A2 | 3/2008 |
| JP | 5403864 B2 | 1/2014 |
| WO | 2011/037394 A2 | 3/2011 |
| WO | 2015/142958 A1 | 9/2015 |
| WO | 2018/119136 A1 | 6/2018 |

*Primary Examiner* — Scott Luan
(74) *Attorney, Agent, or Firm* — Metrolex IP Law Group, PLLC

(57) ABSTRACT

A method of fixing a surgical instrument to a robot arm according to one or more embodiment may include: attaching the surgical instrument to a drive part of the robot arm via an adaptor in a state where a first engagement portion of a drive transmission member of the adaptor is set at a second initial orientation; and rotating the first engagement portion from the second initial orientation so as to engage the first engagement portion of the drive transmission member with an engagement portion of an driven member.

20 Claims, 23 Drawing Sheets

FIRST EMBODIMENT

SURGICAL INSTRUMENT IS MOUNTED BUT NOT ENGAGED

SURGICAL INSTRUMENT IS MOUNTED AND ENGAGED

CROSS SECTION ALONG LINE 101-101

METHOD OF FIXING SURGICAL INSTRUMENT TO ROBOT ARM

CROSS-REFERENCE TO RELATED APPLICATIONS

This application claims priority to Japanese Patent Application No. 2019-062803 filed on Mar. 28, 2019 and Japanese Patent Application No. 2019-187356 filed on Oct. 11, 2019, the entire contents of which are incorporated herein by reference.

BACKGROUND ART

The disclosure may relate to a method of fixing a surgical instrument to a robot arm, and more specifically may relate to a method of fixing a surgical instrument to a robot arm by attaching the surgical instrument to the drive part with or without an adaptor.

In a related art, there has been known a method of fixing a surgical instrument to a drive part of a robot arm by attaching the surgical instrument to the drive part via an adaptor (see for example, Japanese Patent No. 5403864).

Japanese Patent No. 5403864 discloses a method of fixing a surgical instrument to a robot arm to fix the surgical instrument to a spring-loaded input part (drive part) of the robot arm via an instrument sterile adaptor.

The method of fixing the surgical instrument to the robot arm disclosed in Japanese Patent No. 5403864 includes a step of engaging the spring-loaded input part of the robot arm with a disk of the instrument sterile adaptor. With this operation, the spring-loaded input part of the robot arm is attached to the instrument sterile adaptor in such a manner that the disk of the instrument sterile adaptor can be rotated by rotations of the spring-loaded input part.

The method of fixing the surgical instrument to the robot arm disclosed in Japanese Patent No. 5403864 includes a step of engaging a hole (engagement portion) of the disk of the instrument sterile adaptor with a pin (engagement portion) of a disk of the surgical instrument by the spring-loaded input part. With this operation, the surgical instrument is attached to the instrument sterile adaptor in such a manner that the disk of the surgical instrument can be rotated by the rotations of the spring-loaded input part.

The step of engaging the surgical instrument with the instrument sterile adaptor includes a step of rotating the disk of the instrument sterile adaptor with respect to the pin of the disk of the surgical instrument which is placed in an arbitrary position, to thereby engage the pin of the disk of the surgical instrument with the hole of the disk of the instrument sterile adaptor.

SUMMARY

However, in the method of fixing the surgical instrument to the robot arm disclosed in Japanese Patent No. 5403864, an initial position of the pin of the disk of the surgical instrument and an initial position of the hole of the disk of the instrument sterile adaptor may sometimes be arranged too close to each other, so that the pin of the disk of the surgical instrument and the hole of the disk of the instrument sterile adaptor may be unintentionally engaged with each other in an incomplete engagement manner. In this case, even though the engagement between the pin of the disk of the surgical instrument and the hole of the disk of the instrument sterile adaptor is incomplete, a completion of the engagement therebetween may be incorrectly detected.

Therefore, in the method of fixing the surgical instrument to the robot arm disclosed in Japanese Patent No. 5403864, depending of the positional relationship between the initial position of the pin of the disk of the surgical instrument and the initial position of the hole of the disk of the instrument sterile adaptor, the pin of the disk of the surgical instrument and the hole of the disk of the instrument sterile adaptor may get incompletely engaged with each other.

An object of an aspect of the disclosure may be to provide a method of fixing a surgical instrument to a robot arm which is capable of engaging the surgical instrument with an adaptor or the robot arm in a secured and substantially completed engagement manner.

A first aspect of the disclosure may be a method of fixing a surgical instrument to a robot arm by fixing a driven member of the surgical instrument via an adaptor to a drive part of the robot arm for rotating the driven member of the surgical instrument.

The method of fixing the surgical instrument to the robot arm according to the first aspect may include: attaching the surgical instrument to the robot arm via the adaptor in a state where a first engagement portion of the drive transmission member of the adaptor, which is to be engaged with an engagement portion of the driven member, is set in a second initial orientation about a rotational axis, wherein the second initial orientation does not correspond to a first initial orientation in which the engagement portion of the driven member is set; and engaging the first engagement portion of the drive transmission member with the engagement portion of the driven member, by driving the drive part of the robot arm to rotate the first engagement portion of the drive transmission member from the second initial orientation.

A second aspect of the disclosure may be a method of fixing a surgical instrument to a robot arm by fixing a driven member of the surgical instrument to a drive part of the robot arm for rotating the driven member of the surgical instrument.

The method of fixing the surgical instrument to the robot arm according to the second aspect may include: attaching the surgical instrument to the drive part of the robot arm in a state where an engagement portion of the drive part, which is to be engaged with an engagement portion of the driven member, is set in a second initial orientation about a rotational axis, wherein the second initial orientation does not correspond to a first initial orientation in which the engagement portion of the driven member is set; and engaging the engagement portion of the drive part with the engagement portion of the driven member, by driving the drive part of the robot arm to rotate the engagement portion of the drive part from the second initial orientation.

A third aspect of the disclosure may be a method of fixing a surgical instrument to a robot arm by fixing a driven member of the surgical instrument via an adaptor to a drive part of the robot arm for rotating the driven member of the surgical instrument.

The method of fixing the surgical instrument to the robot arm according to the third aspect may include: setting an engagement portion of the drive transmission member of the adaptor, which is to be engaged with an engagement portion of the driven member, to a second initial orientation about a rotational axis, wherein the second initial orientation does not correspond to a first initial orientation in which the engagement portion of the driven member is set; attaching the surgical instrument to the drive part of the robot arm via the adaptor, after the engagement portion of the drive transmission member is set to the second initial orientation; and engaging the engagement portion of the drive transmission member with the engagement portion of the driven member, by driving the drive part of the robot arm to rotate the engagement portion of the drive transmission member from the second initial orientation, after the surgical instrument is attached to the drive part of the robot arm via the adaptor.

DETAILED DESCRIPTION

Figure 1:
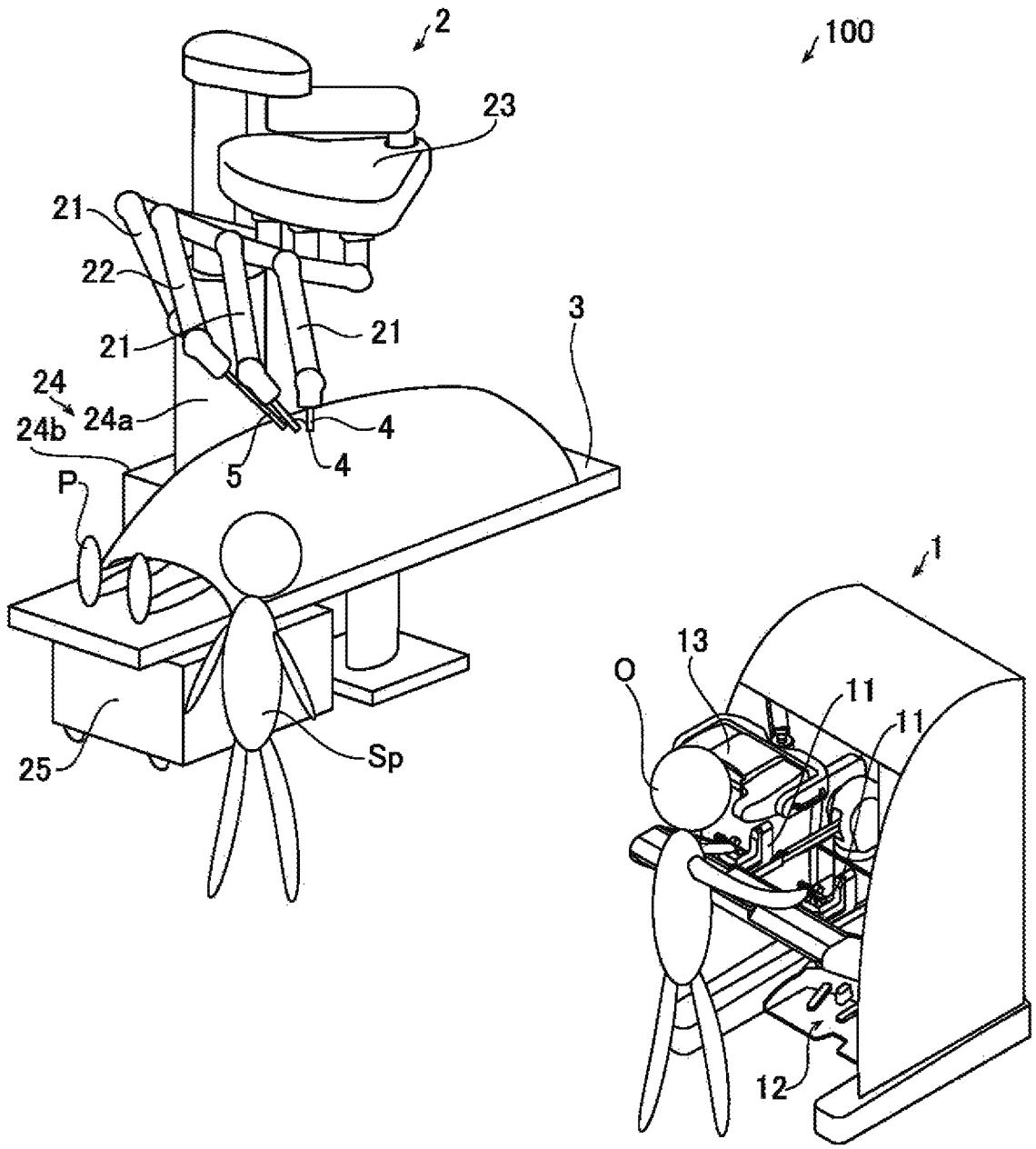
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 1 and a patient-side apparatus 2. The remote control apparatus 1 is provided to remotely control medical equipment provided for the patient-side apparatus 2. When an operator O, as a surgeon, inputs an action mode instruction to be executed by the patient-side apparatus 2, to the remote control apparatus 1, the remote control apparatus 1 transmits the action mode instruction to the patient-side apparatus 2. In response to the action mode instruction transmitted from the remote control apparatus 1, the patient-side apparatus 2 operates medical equipment, including surgical instruments 4 attached to robot arms 21 and an endoscope 5 attached to a robot arm 22. This allows for minimally invasive surgery.

The patient-side apparatus 2 is positioned beside an operation table 3 on which the patient P is laid. The patient-side apparatus 2 constitutes an interface to perform a surgery for a patient P in response to an input from the remote control apparatus 1. The patient-side apparatus 2 includes plural robot arms 21 and 22, a platform 23, a positioner 24, and a controller 25.

Each of the plural robot arms 21 includes plural joints. Each joint includes a driver provided with a servo-motor and a position detector such as an encoder. The robot arms 21 are configured so that the medical equipment attached to each robot arm 21 is controlled by a driving signal given through the controller 25 and performs a desired movement. Note that the robot arm 22 has a configuration same as the robot arm 21.

The surgical instruments 4 as the medical equipment are detachably attached to the distal end portions of the robot arms 21. In surgeries using the patient-side apparatus 2, the robot arms 21 introduce the surgical instruments 4 into the body of the patient P through a cannula (trocar) placed on the body surface of the patient P.

Each surgical instrument 4 includes: a housing 41 (see FIG. 3), which is attached to the robot arm 21; an elongated shaft 42 (see FIG. 3); and an end effector 43 (see FIG. 3), which is provided at the distal end portion of the shaft 42. The end effector 43 may be grasping forceps, scissors, a hook, a high-frequency knife, a snare wire, a clamp, or a stapler, for example. The end effector 43 is not limited to those and can be various types of treatment tools. The end effector 43 of the surgical instrument 4 is then located near the surgery site.

To the distal end portion of the robot arm 22, the endoscope 5 as the medical equipment is detachably attached. The endoscope 5 captures an image within the body cavity of the patient P. The captured image is outputted to the remote control apparatus 1. The endoscope 5 is a 3D endoscope capable of capturing a three-dimensional image or a 2D endoscope. In surgeries using the patient-side apparatus 2, the robot arm 22 introduces the endoscope 5 into the body of the patient P through a trocar placed on the body surface of the patient P. The endoscope 5 is then located near the surgery site.

The platform 23 commonly supports the robot arms 21 and the robot arm 22. The positioner 24 is placed on the floor of an operation room and supports the platform 23. The positioner 24 includes a column 24a including an elevating shaft adjustable in the vertical direction and a base 24b including wheels and thus being movable on the floor surface.

The remote control apparatus 1 constitutes the interface with the operator O. The remote control apparatus 1 is an apparatus that allows the operator O to operate the surgical instruments 4 attached to the robot arms 21 and the endoscope 5 attached to the robot arm 22. Specifically, the remote control apparatus 1 is configured to transmit action mode instructions which are inputted by the operator O and are to be executed by the surgical instruments 4 and endoscope 5, to the patient-side apparatus 2 through the controller 25. The remote control apparatus 1 is installed beside the operation table 3 so that the operator O can see the condition of the patient P very well while operating the remote control apparatus 1, for example. The remote control apparatus 1 may be configured to transmit action mode instructions wirelessly and installed in a room different from the operation room where the operation table 3 is installed.

The action modes to be executed by the surgical instruments 4 include modes of actions to be taken by each surgical instrument 4 (a series of positions and postures) and actions to be executed by the function of each surgical instrument 4. When the surgical instrument 4 is a pair of grasping forceps, for example, the action modes to be executed by the surgical instrument 4 include roll and pitch positions of the wrist of the end effector 43 and actions to open and close the jaws. When the surgical instrument 4 is a high-frequency knife, the action modes to be executed by the surgical instrument 4 may include vibration of the high-frequency knife, specifically, supply of current to the high-frequency knife. When the surgical instrument 4 is a snare wire, the action modes to be executed by the surgical instrument 4 may include a capturing action and an action to release the captured object. Further the action modes may include an action to supply current to a bipolar or monopolar instrument to burn off the surgery site.

The action modes to be executed by the endoscope 5 include, for example, an action mode to move the position and posture of the distal end portion of the endoscope 5 and an action mode to set the zoom magnification, for example.

Figure 2:
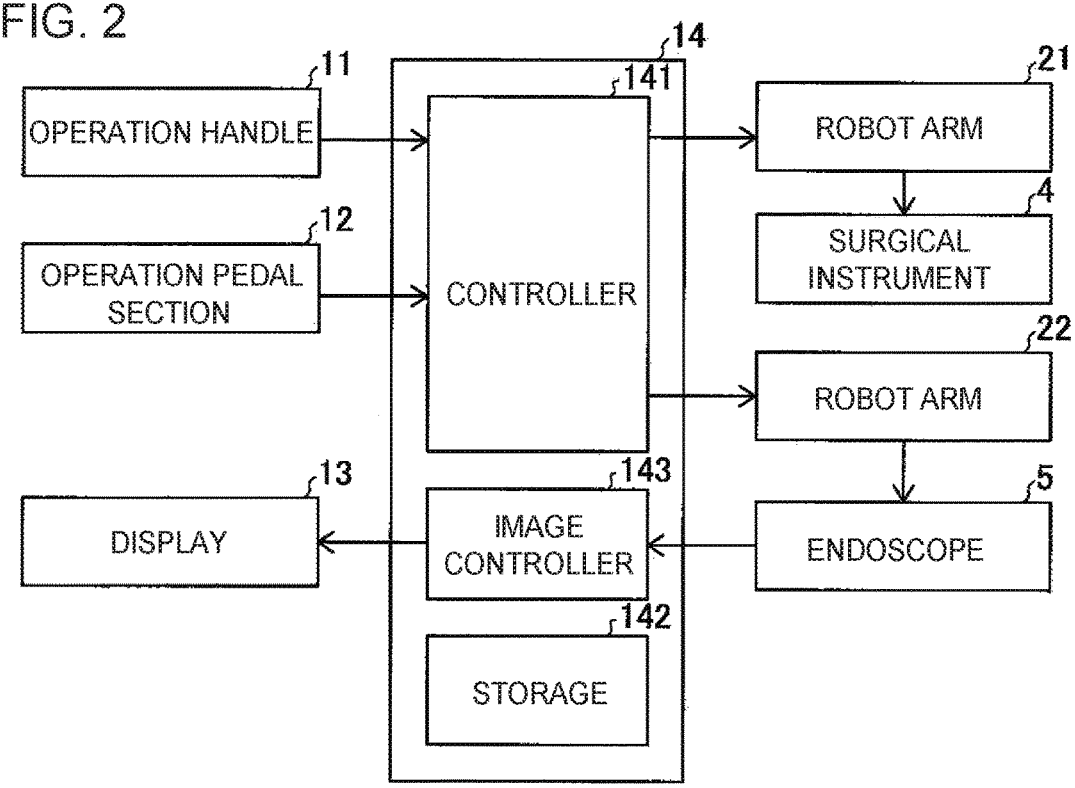
FIG. 2 is a block diagram illustrating a view of a control-related configuration of the robotic surgical system according to a first embodiment.

As illustrated in FIGS. 1 and 2, the remote control apparatus 1 includes operation handles 11, an operation pedal section 12, a display part 13, and a control apparatus 14.

The operation handles 11 are provided in order to remotely operate medical equipment (surgical instruments 4 and the endoscope 5) attached to the robot arms 21 and 22. Specifically, the operation handles 11 accept operations by the operator O for operating the medical equipment. The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 1 toward the front side. The operation handles 11 are configured to move in a predetermined three-dimensional operation region. Specifically, the operation handles 11 are configured so as to move up and down, right and left, and forward and rearward.

The remote control apparatus 1 and patient-side apparatus 2 constitute a master-slave system in terms of controlling movement of the robot arms 21 and 22. The operation handles 11 constitute an operating part on the master side in the master-slave system. The robot arms 21 and 22 holding medical equipment constitute an operating section on the slave side. When the operator O operates the operation handles 11, the movement of the robot arms 21 or 22 is controlled so that the distal end portions (the end effectors 43 of the surgical instruments 4) of the robot arms 21 or the distal end portion (the endoscope 5) of the robot arm 22 moves following the movement of the operation handles 11.

The patient-side apparatus 2 controls the movement of the robot arms 21 in accordance with the set motion scaling ratio. When the motion scaling ratio is set to ½, for example, the end effectors 43 of the surgical instruments 4 move ½ of the movement distance of the operation handles 11. This allows for precise fine surgery.

The operation pedal section 12 includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 4 to coagulate a surgery site. Specifically, when the coagulation pedal is operated, voltage for coagulation is applied to the surgical instrument 4 to coagulate a surgery site. The cutting pedal enables the surgical instrument 4 to cut a surgery site. Specifically, the cutting pedal is operated to apply voltage for cutting to the surgical instrument 4 and cut a surgery site.

The camera pedal is used to control the position and orientation of the endoscope 5 that captures images within the body cavity. Specifically, the camera pedal enables operation of the endoscope 5 by the operation handles 11. The position and orientation of the endoscope 5 are controllable by the operation handles 11 while the camera pedal is being pressed. The endoscope 5 is controlled by using both of the right and left operation handles 11, for example. Specifically, when the operator O rotates the right and left operation handles 11 about the middle point between the right and left operation handles 11, the endoscope 5 is rotated. When the operator O presses the right and left operation handles 11 together, the endoscope 5 goes forward into the body cavity. When the operator O pulls the right and left operation handles 11 together, the endoscope 5 goes back. When the operator O moves the right and left operation handles 11 together up, down, right, or left, the endoscope 5 moves up, down, right, or left, respectively.

The clutch pedal is used to temporarily disconnect operation-related connection between the operation handles 11 and the robot arms 21 and 22 to stop movement of the surgical instruments 4. Specifically, when the clutch pedal is being pressed, the robot arms 21 and 22 of the patient-side apparatus 2 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21 and 22. The operator O restarts the operation for the operation handles 11 around the center thereof.

The display part 13 or a display is configured to display images captured by the endoscope 5. The display part 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 5 attached to the robot arm 22 of the patient-side apparatus 2. When the non-scope type display section is attached, the non-scope type display section also displays 3D images captured by the endoscope 5 provided for the patient-side apparatus 2. The non-scope type display section may display 2D images captured by the endoscope 5 provided for the patient-side apparatus As illustrated in FIG. 2, the control apparatus 14 includes a controller 141, a storage 142, and an image controller 143, for example. The controller 141 includes a calculator such as a CPU. The storage 142 includes a memory, such as a ROM (Read Only Memory) and a RAM (Random Access Memory). The control apparatus 14 may be composed of a single controller performing centralized control or may be composed of plural controllers that perform decentralized control in cooperation with each other.

The controller 141 determines whether an action mode instruction inputted by the operation handles 11 is to be executed by the surgical instruments 4 or to be executed by the endoscope 5, depending on the state of the operation pedal section 12. When determining that the action mode instruction inputted by the operation handles 11 is to be executed by any one of the surgical instruments 4, the controller 141 transmits the action mode instruction to the corresponding robot arm 21. The robot arm 21 is thereby driven for controlling movement of the surgical instrument 4 attached to the robot arm 21.

When determining that the action mode instruction inputted by the operation handles 11 is to be executed by the endoscope 5, the controller 141 transmits the action mode instruction to the robot arm 22. The robot arm 22 is thereby driven for control of movement of the endoscope 5 attached to the robot arm 22.

The storage 142 stores control programs corresponding to the types of the surgical instrument 4, for example. The controller 141 reads the stored control programs according to the types of the attached surgical instruments 4. The action mode instruction from at least one of the operation handles 11 and the operation pedal section 12 of the remote control apparatus 1 thereby cause the respective surgical instruments 4 to perform proper movements.

The image controller 143 transmits images acquired by the endoscope 5 to the display part 13. The image controller 143 performs processing and alternations for the images when needed.

(Configuration of Surgical Instrument, Adaptor, Drape, and Robot Arm)

With reference to FIGS. 3 to 11, the configurations of the surgical instrument 4, an adaptor 6a to which a stopper 6b is attached (hereinafter, may be referred to as stopper-attached adaptor 6), a drape 7, and the robot arm 21 are described.

Here, the direction in which the surgical instrument 4 (the direction in which the shaft 42 extends) is defined as a Y direction, the distal side of the surgical instrument 4 along the Y direction is defined as a Y1 direction, and the opposite side of the Y1 direction is defined as a Y2 direction. The direction in which the surgical instrument 4 and the adaptor 6a are adjacent to each other is defined as a Z direction, the surgical instrument 4 side along the Z direction is defined as a Z1 direction, and the opposite side of the Z1 direction is defined as a Z2 direction. Further, the direction orthogonal to the Y direction and the Z direction is defined as an X direction, one side along the X direction is defined as an X1 direction, and the other side along the X direction is defined as an X2 direction.

(Attached State)

Figure 3:
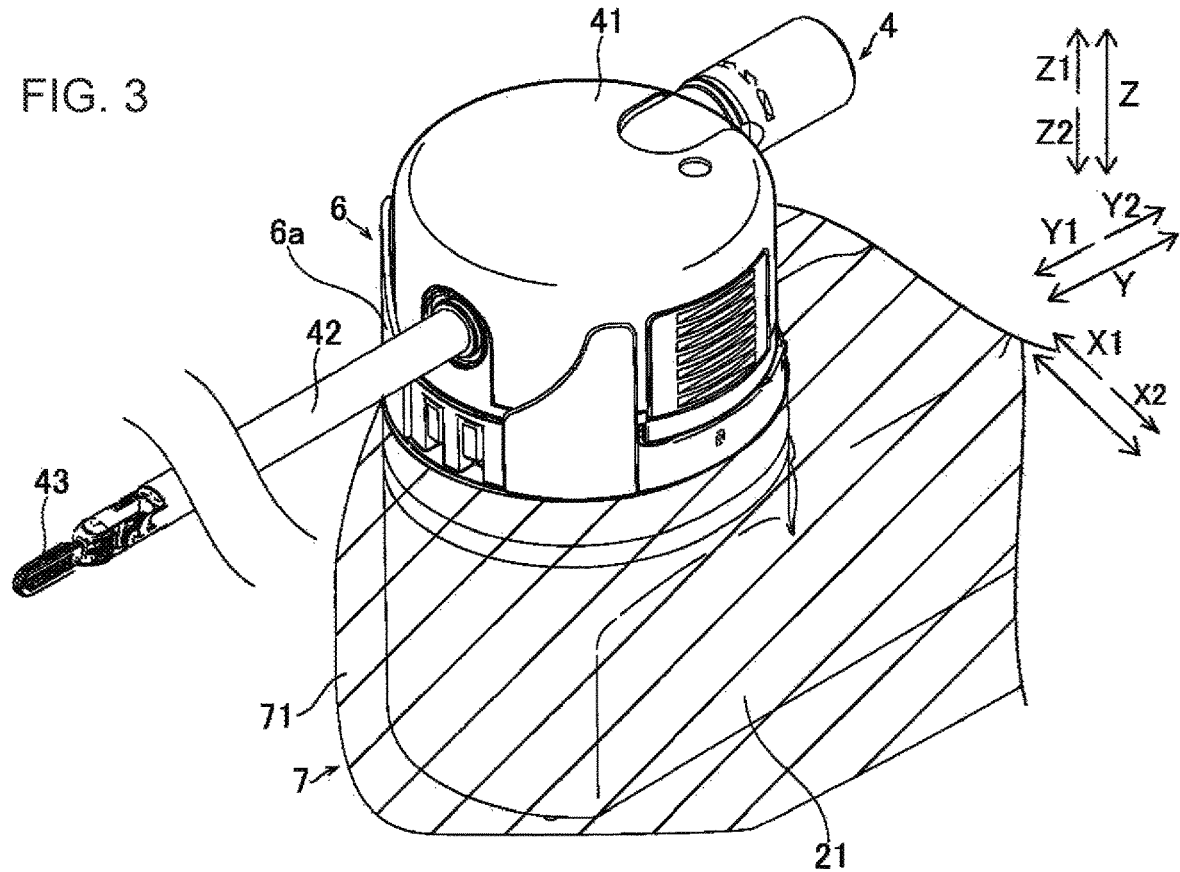
FIG. 3 is a diagram illustrating a perspective view of a state where a surgical instrument is attached to a robot arm via an adaptor according to a first embodiment.
Figure 4:
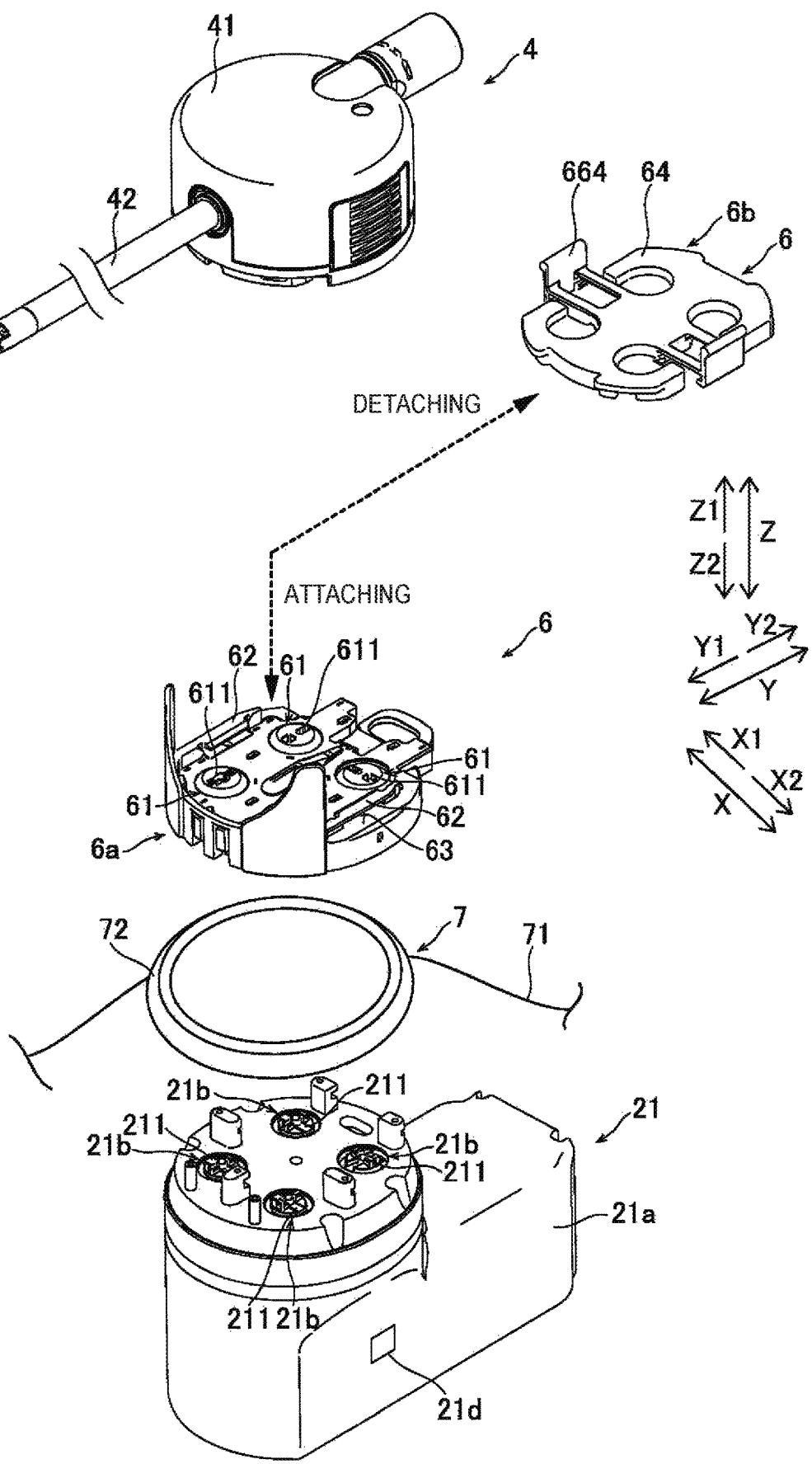
FIG. 4 is a diagram illustrating an exploded perspective view of a state where the surgical instrument is to be attached to the robot arm via the adaptor according to a first embodiment.

As illustrated in FIGS. 3 to 4, the surgical instrument 4 is detachably connected to the robot arm 21 through the adaptor 6a. The adaptor 6a is a drape adaptor configured to sandwich a sterile drape 7 to cover the robot arm 21, between the robot arm 21 and the adaptor 6a. That is, the adaptor 6a is configured such that the drape 7 is attachable to the adaptor 6a.

The surgical instrument 4 is attached to the Z1 side of the adaptor 6a. The adaptor 6a is attached to the Z1 side of the robot arm 21.

The robot arm 21 is used in the clean area and is thus covered with the drape 7. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O and an assistant Sp (see FIG. 1), make sure that only sterile objects are placed in the clean area during surgery and perform sterilization for an object which is to be moved to the clean area from the contaminated area. Similarly, when the assistant Sp, as one of the members of the surgical team including the operator O, place their hands in the contaminated area, the members sterilize their hands before directly touching objects located in the clean area. Instruments used in the clean area are sterilized or are covered with sterile drape 7.

As illustrated in FIG. 4, the drape 7 includes a body section 71 that covers the robot arm 21 and an attachment section 72 sandwiched between the robot arm 21 and the adaptor 6a. The body section 71 is made of a flexible film member. The flexible film member is made of a resin material, such as thermoplastic polyurethane and polyethylene. The body section 71 includes an opening so that the robot arm 21 is engaged with the adaptor 6a. In the opening of the body section 71, the attachment section 72 is provided so as to close the opening. The attachment section 72 is made of a resin mold member. The resin mold member is made of a resin member such as polyethylene terephthalate. The attachment section 72 is harder (less flexible) than the body section 71. The attachment section 72 includes an opening so that the robot arm 21 is engaged with the adaptor 6a. The opening of the attachment section 72 may be provided corresponding to the section where the robot arm 21 is engaged with the adaptor 6a. The opening of the attachment section 72 may include plural openings corresponding to plural sections at which the robot arm 21 is engaged with the adaptor 6a.

Figure 5:
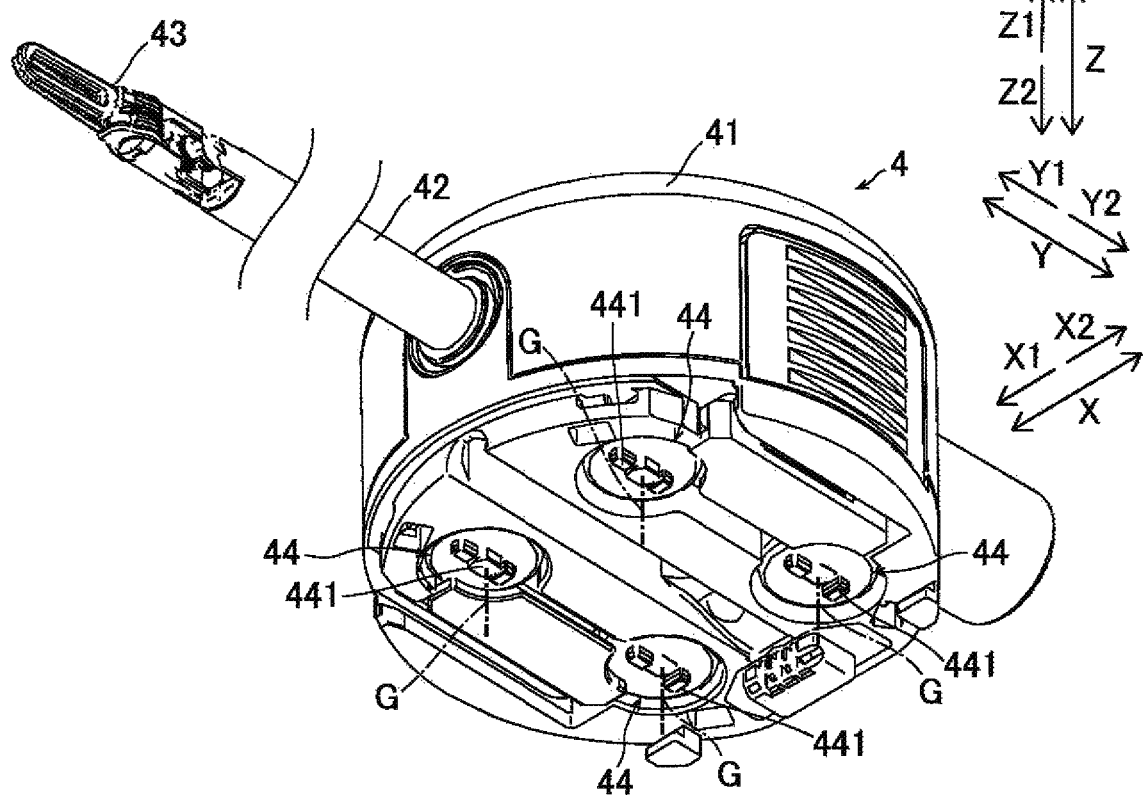
FIG. 5 is a diagram illustrating a perspective view of the surgical instrument according to a first embodiment.

As illustrated in FIGS. 4 and 5, the surgical instrument 4 includes plural (four) driven members 44. The driven members 44 are provided within the housing 41 and are rotatable about the respective rotation axes G extending along the Z axis. The plural driven members 44 are provided to operate (drive) the end effector 43. For example, the driven members 44 are connected to the end effector 43 with wires (not illustrated) inserted through the shaft 42. With this, rotations of the driven members 44 drive the wires, which operate (drive) the end effector 43. In addition, the driven member 44 is connected to the shaft 42 through gears (not illustrated), for example. With this, the shaft 42 is rotated with rotation of the driven member 44.

To transmit driving forces from the robot arm 21 to the end effector 43, the driven members 44 include engagement projections 441, which are engaged with later-described drive transmission members 61 of the adaptor 6a. The engagement projections 441 protrude from the Z2-side surfaces of the respective driven members 44 toward the adaptor 6a (in the Z2 direction). Each of the engagement projections 441 includes plural projected portions linearly arranged. The engagement projections 441 have shapes corresponding to those of later-described engagement recesses 611 (see FIG. 4) of the adaptor 6a, respectively. Each of the engagement projections 441 has a line-symmetric shape. The engagement projection 441 is an example of an engagement portion of a driven member.

Figure 6:
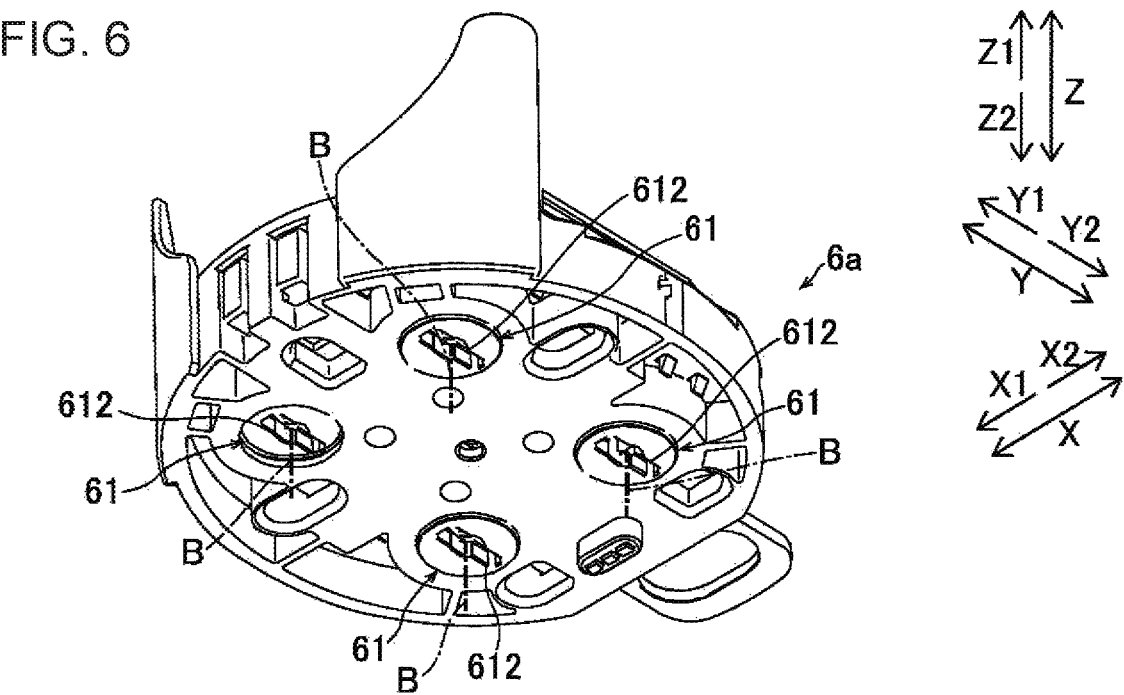
FIG. 6 is a diagram illustrating a perspective view of an adaptor according to the first embodiment.

As illustrated in FIGS. 4 and 6, the adaptor 6a includes plural (four) drive transmission members 61 and a pair of guide rails 62. The drive transmission members 61 are configured to transmit driving forces from the robot arm 21 to the driven members 44 of the surgical instrument 4. That is, the drive transmission members 61 are provided so as to correspond to the driven members 44 of the surgical instrument 4. The drive transmission members 61 are rotatable about the respective rotation axes B, which extend along the Z direction.

As illustrated in FIG. 4, each of the drive transmission members 61 includes the engagement recess 611 which is respectively engaged with the engagement projection 441 of the corresponding driven member 44. The engagement recess 611 is located at the surgical instrument 4 side (the Z1 side) of the drive transmission member 61 and is recessed from the Z1 side surface of the drive transmission member 61, toward the Z2 direction, opposite to the surgical instrument 4. Each of the engagement recesses 611 has a line-symmetric shape. The engagement recess 611 is an example of a first engagement portion of a drive transmission member.

As illustrated in FIG. 6, each of the drive transmission members 61 includes an engagement recess 612, which is engaged with a later-described engagement projection 211 of the corresponding drive part 21b of the robot arm 21. The engagement recess 612 is located at the robot arm 21 side (the Z2 side) of the drive transmission member 61. The engagement recess 612 is recessed from the Z2 side surface of the drive transmission member 61, toward the Z1 direction, opposite to the robot arm 21. The plural drive transmission members 61 include substantially the same configuration. Each of the engagement recesses 612 has a line-symmetric shape. The engagement recess 612 is an example of a second engagement portion of a drive transmission member.

Figure 7A:
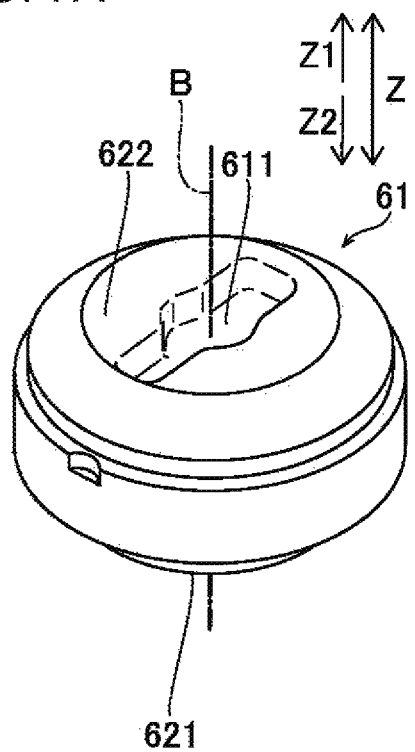
FIG. 7A is a diagram illustrating a perspective view of a drive transmission member.
Figure 7B:
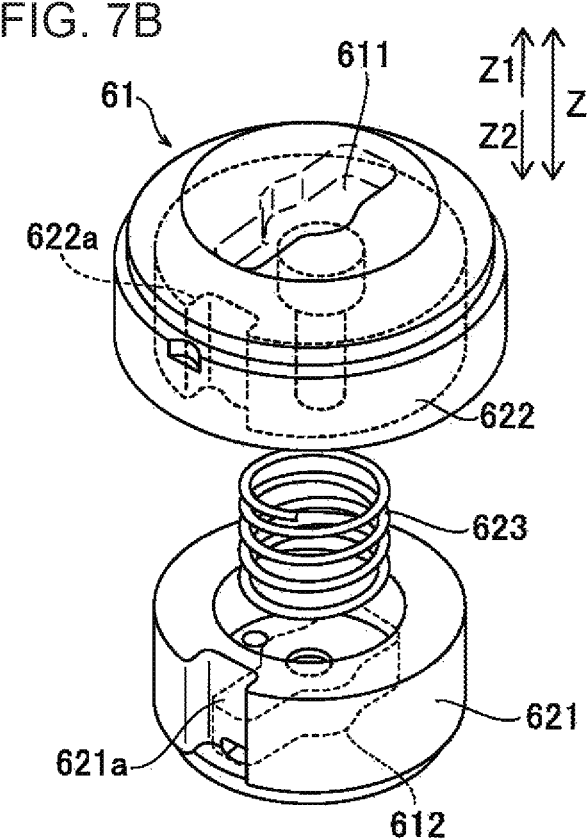
FIG. 7B is a diagram illustrating an exploded perspective view of the drive transmission member.

As illustrated in FIGS. 7A and 7B, each of the drive transmission members 61 includes a first member 621, which includes the engagement recess 612, and a second member 622, which includes the engagement recess 611. The first member 621 is located on the robot arm 21 side (the Z2 side) with respect to the second member 622 and the second member 622 is located on the surgical instrument 4 side (the Z1 side) with respect to the first member 621.

The first member 621 and the second member 622 accommodate a spring 623 therebetween. The spring 623 biases the first member 621 toward the Z2 side and the second member 622 toward the Z1 side. The spring 623 is a compression spring (a compression coil spring). The first member 621 is movable along the Z direction relative to the second member 622 with the spring 623 therebetween. The second member 622 is movable along the Z direction relative to the first member 621 with the spring 623 therebetween.

The first member 621 and the second member 622 are integrally rotated with each other about the rotational axis B extending the Z direction. Specifically, the first member 621 includes an engagement recess 621a that is engaged with the second member 622 with respect to the rotational direction, and the second member 622 includes an engagement protrusion 622a that is engaged with the first member 621 with respect to the rotational direction.

As illustrated in FIG. 4, the pair of guide rails 62 is configured to guide a sliding movement of the surgical instrument 4 in the Y1 direction upon attaching the surgical instrument 4 to the adaptor 6a. Specifically, the pair of guide rails 62 is provided on the Z1 side surface 63 of the adaptor 6a. The pair of guide rails 62 is provided to extend along the Y direction. The guide rails 62 are opposed to each other in the X direction.

Figure 8:
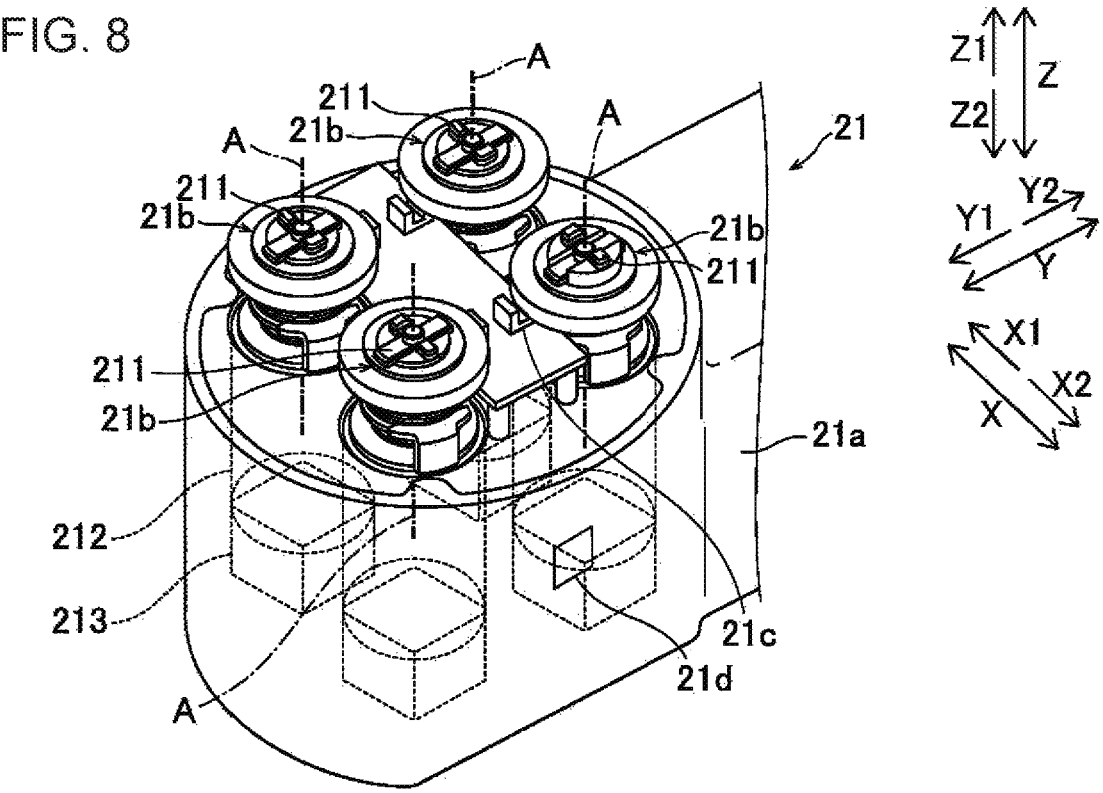
FIG. 8 is a diagram illustrating a perspective view of a drive part of the robot arm according to a first embodiment.

As illustrated in FIGS. 4 and 8, the robot arm 21 includes a frame 21a, a plurality (four) of the drive part 21b, an optical sensor 21c, and a lamp 21d. Each of the drive parts 21b is attached to the frame 21a of the robot arm 21. The plural drive parts 21b are provided corresponding to the plurality (four) of the drive transmission members 61 of the adaptor 6a. Each of the drive parts 21b has the same or a similar configuration, and thus only one of the drive parts 21b is described below to avoid redundancy.

Figure 9A:
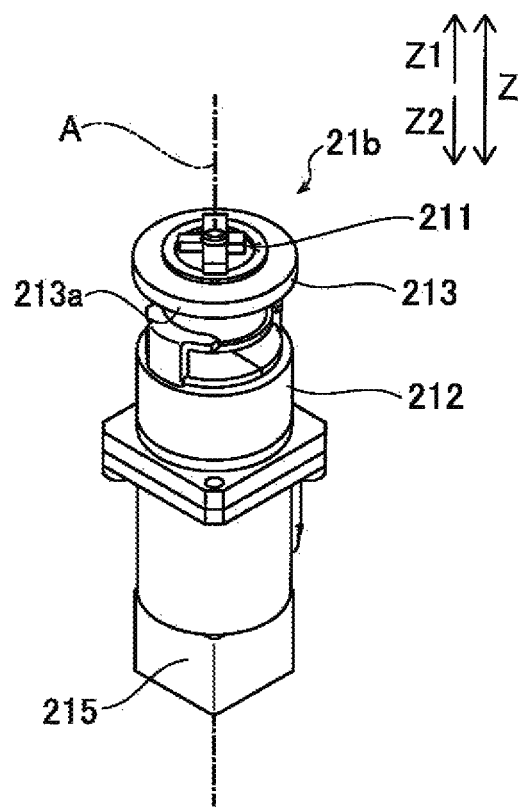
FIG. 9A is a diagram illustrating a perspective view of the drive part.
Figure 9B:
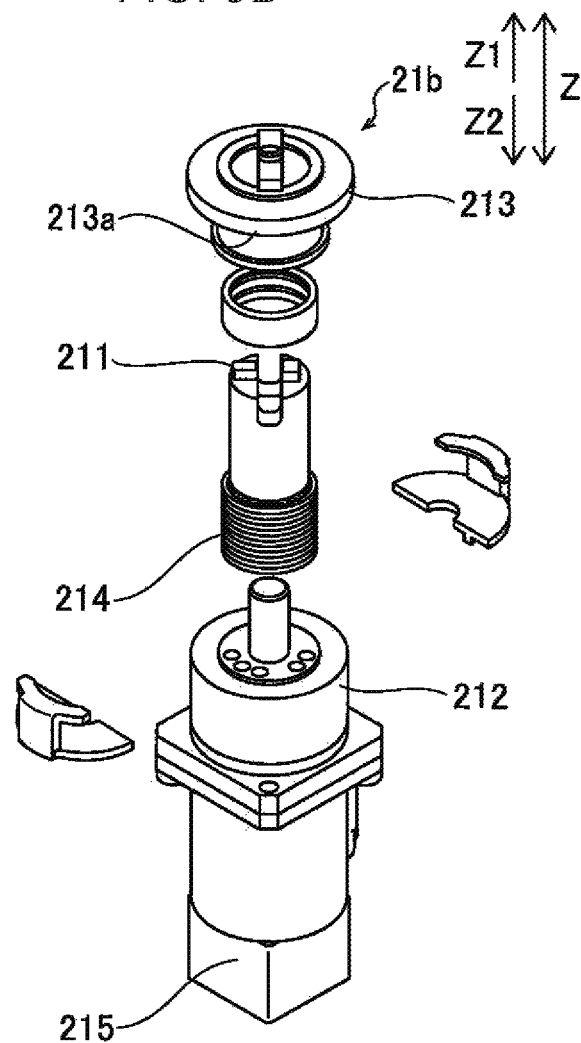
FIG. 9B is a diagram illustrating an exploded perspective view of the drive part.

As illustrated in FIGS. 9A and 9B, the drive part 21b includes the engagement projection 211, an actuator 212, a detection member 213, a spring 214, and an encoder 215. The engagement projection 211 is an example of an engagement portion of a drive part.

The detection member 213 is provided to be detected by the optical sensor 21c. That is, the detection member 213 is configured to move along with the movement of the second member 622 of the drive transmission member 61 in the Z direction. The detection member 213 includes a light blocking part 213a that blocks light emitted from the optical sensor 21c when the second member 622 of the drive transmission member 61 is moved in the Z2 direction. The light blocking part 213a is provided on an outer periphery of the detection member 213. The light blocking part 213a protrudes toward the Z2 direction. Note that the light blocking part 213a is configured not to block the light emitted from the optical sensor 21c when the second member 622 of the drive transmission member 61 is moved in the Z1 direction.

The engagement projection 211 of each drive part 21b is engaged with the engagement recess 612 of the corresponding drive transmission member 61 (see FIG. 6). The engagement projection 211 projects from the Z1 side surface of the drive part 21b toward the Z1 direction (the adaptor 6a side). Each of the engagement projections 211 has a line-symmetric shape.

The actuator 212 includes a motor. The actuator 212 is configured to rotate the engagement projection 211 about the rotational axis A extending in the Z direction. Thereby, the drive transmission member 61 of the adaptor 6a engaged with the engagement projection 211 can be rotated about the rotational axis B, and the driven member 44 of the surgical instrument 4 engaged with the drive transmission member 61 can be rotated about the rotational axis G. Note that the rotational axes A, B, and G are coaxially disposed.

The encoder 215 detects the rotation angle of the shaft of the motor of the actuator 212. The encoder 215 is used to detect the rotation speed of the shaft based on the rotation angle of the shaft. An absolute rotary encoder is preferably used as the encoder 215 to detect the current rotation angle of the shaft of the motor.

Here, the controller 141 is configured to detect the completion of the engagement between the robot arm 21 and the adaptor 6a based on a change in the rotation speed based on the rotation angle of the shaft of the motor detected by the encoder 215. For example, when the rotation speed of the shaft of the motor detected by the encoder 215 becomes equal to or less than a threshold value (for example, 5 [rpm]), the controller 141 detects (determines) that the completion of the engagement between the robot arm 21 and the adaptor 6a. Further, the controller 141 is configured, after the detection of the completion of the engagement between the robot arm 21 and the adaptor 6a, to reverse the rotational direction of the drive parts 21b to rotate the drive parts 21b in the reversed rotational direction opposite to the rotational direction of the drive parts 21b before the detection of the completion of the engagement. More specifically, the controller 141 rotates the drive parts 21b in the reversed rotational direction opposite to the rotational direction of the drive parts 21b before the detection of the completion of the engagement, by a rotational angle (misaligned rotational angle) between a target rotational position of the engagement projections 211 of the drive parts 21b and an actual rotational position of the engagement projections 211 of the drive parts 21b when the completion of the engagement between the robot arm 21 and the adaptor 6a is detected.

Figure 10A:
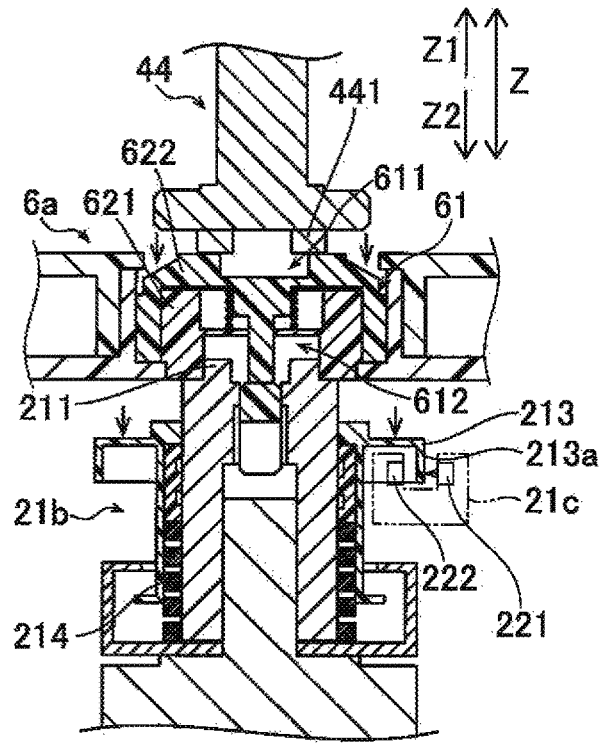
FIG. 10A is a diagram illustrating a cross-sectional view of a state where the surgical instrument and the adaptor are not engaged.
Figure 10B:
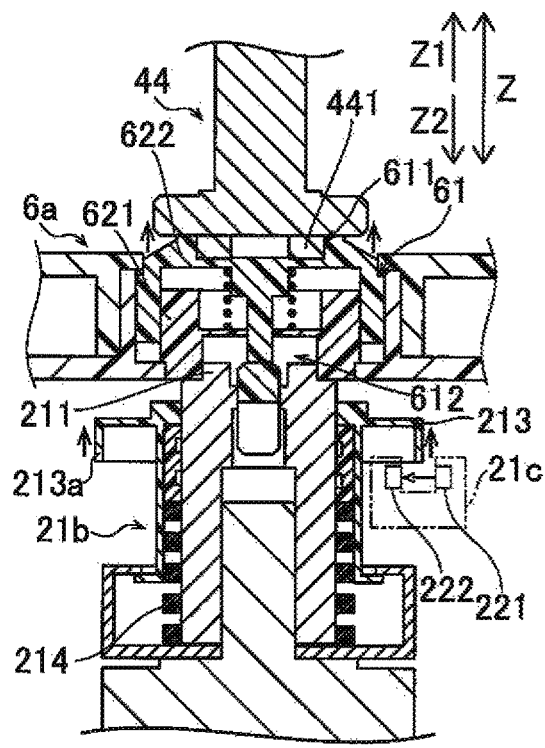
FIG. 10B is a diagram illustrating a cross-sectional view of a state where the surgical instrument and the adaptor are completely engaged.

As illustrated in FIGS. 10A and 10B, the optical sensor 21c is configured to detect the completion of the engagement between the adaptor 6a and the surgical instrument 4, by using the change in the amount of received light according to the movement of the detection member 213 in the Z direction. For example, the optical sensor 21c may be a light transmission type sensor including a light emission part 221 that emits light and a light reception part 222 that receives the light from the light emission part 221.

When the light blocking part 213a of the detection member 213 moves in the Z direction along with the movement of the detection member 213 in the Z direction, which makes the optical sensor 21c transitioning from a light-blocked state to a light-unblocked state, the optical sensor 21c detects the completion of the engagement between the adaptor 6a and the surgical instrument 4. Specifically, as illustrated in FIG. 10A, when the engagement projection 441 and the engagement recess 611 are not engaged and the second member 622 is located in the Z2 side, the light emitted from the light emission part 221 toward the light reception part 222 is blocked by the light blocking part 213a. Thus, the optical sensor 21c detects incompletion of the engagement between the adaptor 6a and the surgical instrument 4. In contrast, as illustrated in FIG. 10B, when the engagement projection 441 and the engagement recess 611 are engaged and the second member 622 is located in the Z1 side, the light irradiated from the light emission part 221 toward the light reception part 222 is not blocked by the light blocking part 213a. Thus, the optical sensor 21c detects the completion of the engagement between the adaptor 6a and the surgical instrument 4. Note that the optical sensor 21c is configured to detect High when the light is received and to detect Low when the light is blocked.

The controller 141 is configured, in response to the detection of the completion of the engagement between the adaptor 6a and the surgical instrument 4, to further rotate the drive parts 21b by a predetermined rotational angle while maintaining the rotational direction of the drive transmission member 61. More specifically, the controller 141 is configured to overrun (further rotate) the drive parts 21b by the predetermined rotational angle, which is an angle (misaligned angle) between a target rotational position of the engagement projections 211 of the drive parts 21b and an actual rotational position of the engagement projections 211 of the drive parts 21b when the completion of the engagement between the robot arm 21 and the adaptor 6a is detected by the optical sensor 21c.

The lamp 21d is configured to change the lighting state thereof depending on the detection results of the completion of the engagement between the robot arm 21 and the adaptor 6a and the completion of the engagement between the adaptor 6a and the surgical instrument 4.

Specifically, the lamp 21d is configured to be turned on (to emit light) when the engagement between the robot arm 21 and the adaptor 6a is completed, and to be turned off (to emit no light) when the robot arm 21 and the adaptor 6a are not yet completely engaged. Note that the lamp 21d is configured to be turned on (to emit light) when the engagement between the robot arm 21 and the adaptor 6a is completed and then turned off (to emit no light).

The lamp 21d is configured to be turned on (to emit light) when the adaptor 6a and the surgical instrument 4 are completely engaged, and to be turned off (to emit no light) when the adaptor 6a and the surgical instrument 4 are not yet completely engaged. Note that the lamp 21d is configured to be turned on (to emit light) when the engagement between the adaptor 6a and the surgical instrument 4 is completed and then turned off (to emit no light).

Note that the lamp 21d may be configured to emit light of a first color such as green when both of the engagement between the robot arm 21 and the adaptor 6a and the engagement between the adaptor 6a and the surgical instrument 4 are completed, and be configured to emit light of a second color such as red different from the first color, instead of turning off the light, when neither of the engagement between the robot arm 21 and the adaptor 6a nor the engagement between the adaptor 6a and the surgical instrument 4 are completed. In addition, the lamp 21d may be configured such that a color of the light emitted from the lamp 21d when the engagement between the robot arm 21 and the adaptor 6a is completed is different from a color of the light emitted from the lamp 21d when the engagement between the adaptor 6a and the surgical instrument 4 is completed.

(Configuration of Stopper)

As illustrated in FIG. 4, the stopper-attached adaptor 6 includes the adaptor 6a and a stopper 6b attached to the adaptor 6a, wherein the adaptor 6a is to be provided between the drive parts 21b and the surgical instrument 4 and includes the drive transmission members 61 rotatable therein to transmit the driving forces from the drive parts 21b to the surgical instrument 4.

Figure 11:
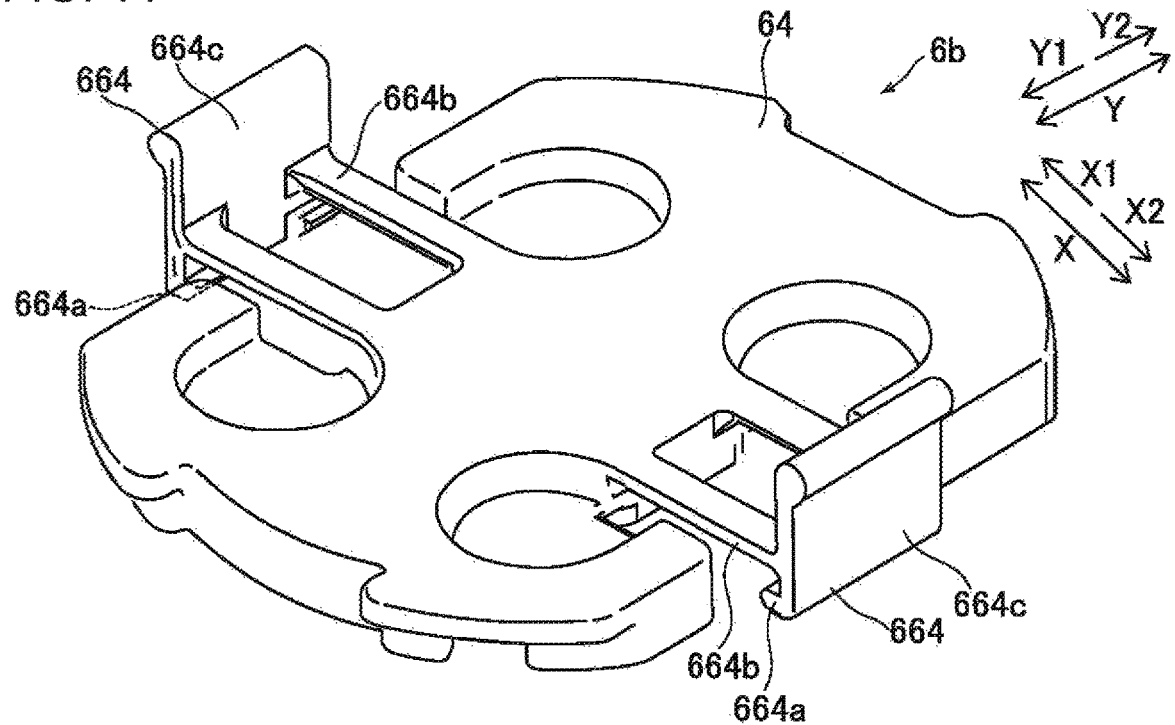
FIG. 11 is a diagram illustrating a perspective view of a stopper according to a first embodiment as viewed from the Z1 side.
Figure 12:
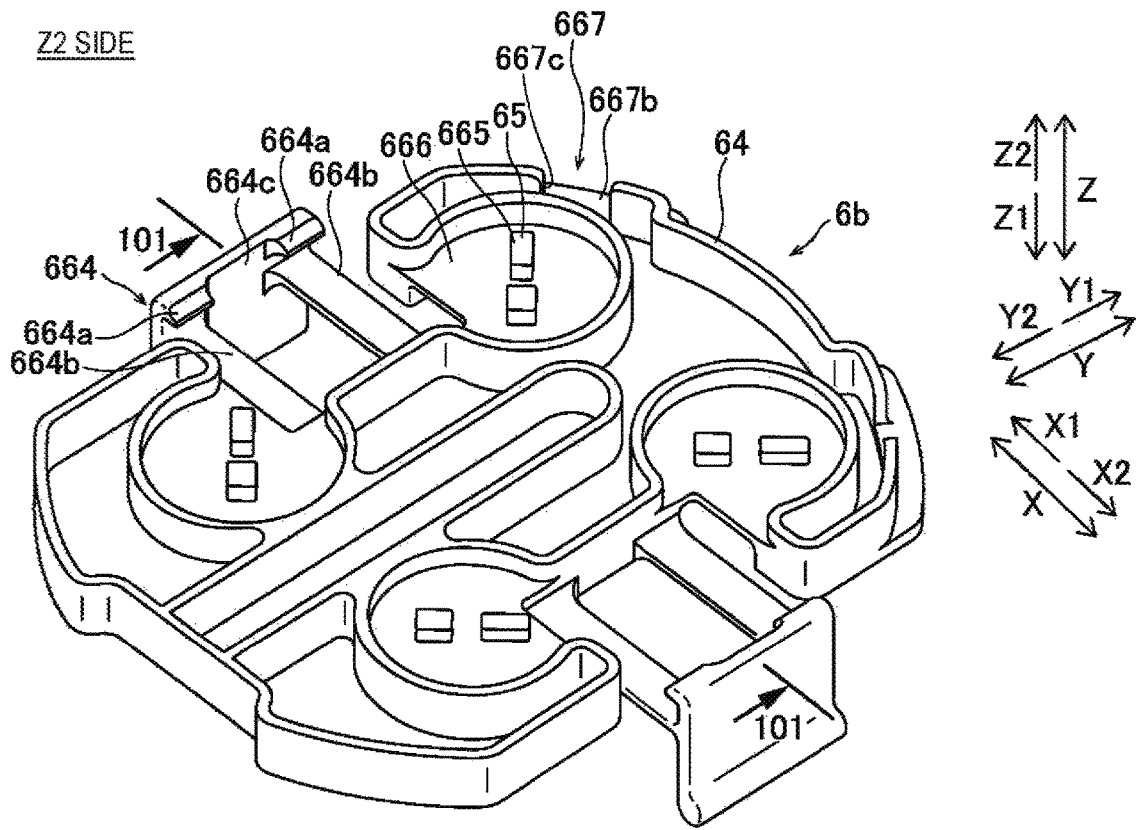
FIG. 12 is a diagram illustrating a perspective view of the stopper according to a first embodiment as viewed from the Z2 side.

As illustrated in FIGS. 11 and 12, the stopper 6b is configured to hold the adaptor 6a with fixing and holding rotational angles of the drive transmission members 61 of the adaptor 6a (see FIG. 4).

Specifically, the stopper 6b includes a stopper body 64 and rotation restriction portions 65 provided on the stopper body 64 to regulate the rotations of the drive transmission members 61 (see FIG. 4). The stopper body 64 is configured to be attached to the adaptor 6a with the rotation restriction portions 65 restricting the rotations of the drive transmission members 61, upon attaching the adaptor 6a to the drive parts 21b (see FIG. 4) of the robot arm 21. The stopper body 64 is also configured to be detached from the adaptor 6a after the adaptor 6a is attached to the drive parts 21b of the robot arm 21.

The stopper body 64 is formed of a resin material such as polypropylene. The stopper body 64 is formed with a reduced thickness. When viewed from the Z1 side, the stopper body 64 has a shape corresponding to the Z1 side surface 63 (see FIG. 4) of the adaptor 6a. The Z1 side surface 63 of the stopper body 64 is formed in a substantially planar shape. The Z2 side surface of the stopper body 64 has projections and recesses to reduce the thickness.

(Configuration of Attachment Portion)

The stopper body 64 includes an attachment portion 664 for detachably attaching the stopper body 64 to the adaptor 6a (see FIG. 4).

In other words, the attachment portion 664 is configured to attach the stopper body 64 to the adaptor 6a with fixing the position of the stopper body 64 with respect to the adaptor 6a, and to detach the stopper body 64 from the adaptor 6a with releasing the fixation of the position of the stopper body 64 with respect to the adaptor 6a. For example, the attachment portion 664 includes a pair of engagement portions 664a, a pair of resiliently deformable portions 664b, and a pair of grab portions 664c.

The attachment portion 664 is configured to restrict movements of the stopper body 64 relative to the adaptor 6a (see FIG. 4) in a state where the adaptor 6a is attached to the stopper body 64.

Figure 13:
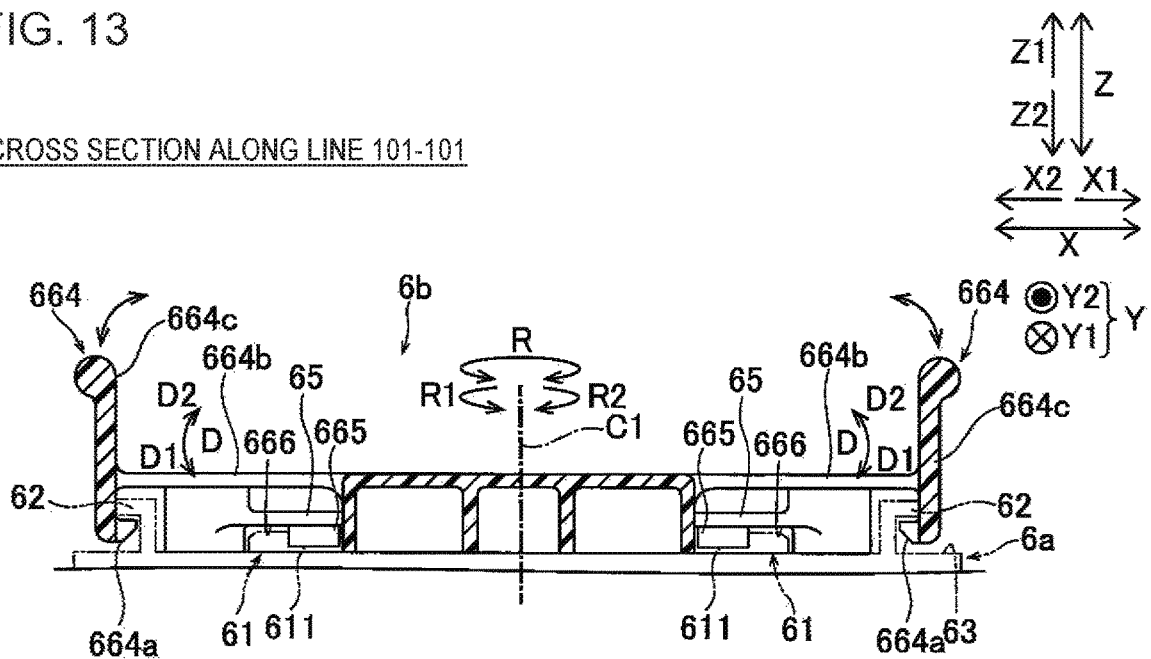
FIG. 13 is a diagram illustrating a sectional view taken along line 101-101 of FIG. 12.

Specifically, as illustrated in FIGS. 12 and 13, the pair of engagement portions 664a of the attachment portion 664 is configured to be detachably engaged with the adaptor 6a and to restrict the movements of the stopper body 64 relative to the adaptor 6a.

The pair of engagement portions 664a is configured to restrict the movements of the stopper body 64 in the Z direction and the rotations of the stopper body 64 about the center axis C1 of the stopper body 64 parallel to the Z direction. Here, in the direction (X direction) in which the grab portions 664c are opposed to each other, each of the pair of engagement portions 664a is projected toward the center axis C1 from the inner surfaces of the pair of grab portions 664c on the center axis C1 side. In the direction (the Z direction) in which the adaptor 6a and the stopper 6b are adjacent to each other, the pair of engagement portions 664a is formed at portions of the grab portions 664c on the side of the adaptor 6a, respectively. Each of the pair of engagement portions 664a is divided in plural (two) pieces arranged in the direction (the Y direction) in which the surgical instrument 4 extends. The pair of engagement portions 664a contacts with the movement restriction surface of the adaptor 6a from the Z2 side and thereby restricts the movement of the stopper body 64 in the Z direction.

Specifically, the pair of engagement portions 664a is detachably engaged with the pair of guide rails 62 (see FIG. 4) provided at the adaptor 6a, wherein the pair of guide rails 62 is configured to guide attaching of the surgical instrument 4 to the adaptor 6a.

The movements of the stopper body 64 in the Z direction are restricted by contacting the Z1 side portions of the engagement portions 664a with the portions of the guide rails 62 facing the engagement portions 664a. The rotations of the stopper body 64 about the center axis C1 are restricted, by contacting, in the X direction, the C1 side portions of the engagement portions 664a with the portions of the guide rails 62 on the opposite side of the center axis C1.

Each of the pair of resiliently deformable portions 664b is configured to be resiliently deformed along with movements of the pair of grab portions 664c. Here, in the direction (the X direction) in which the grab portions 664c are opposed to each other, the pair of resiliently deformable portions 664b connects the pair of grab portions 664c with the stopper body 64. Each of the resiliently deformable portions 664b is formed in a thin plate shape in the direction (the Z direction) in which the adaptor 6a and the stopper 6b are adjacent to each other. Each of the resiliently deformable portions 664b is resiliently deformable in the circumferential direction D about the center axis C2 (see FIG. 13) of the stopper body 64 parallel to the longitudinal direction (the Y direction) of the surgical instrument 4, toward the direction D1 which is one side of the circumferential direction D and toward the direction D2 which is the other side of the circumferential direction D. The thickness of each of the resiliently deformable portions 664b is less than the thickness of each of the grab portions 664c.

The attachment portion 664 of the stopper body 64 is configured, when the stopper body 64 is moved to the adaptor 6a along the direction (the Z direction) orthogonal to the Z1 side surface 63 of the adaptor 6a, to attach the stopper body 64 to the adaptor 6a, and is configured, when the stopper body 64 is moved away from the adaptor 6*a* in the Z direction, to detach the stopper body 64 from the adaptor 6*a*.

Specifically, the pair of grab portions 664*c* of the attachment portion 664 is configured to move the pair of engagement portions 664*a* in the direction D2 away from the adaptor 6*a* or the direction D1 closer to the adaptor 6*a* by elastically deforming a part of the stopper body 64.

That is, by the movement of the pair of engagement portions 664*a* along with the movement of the pair of grab portions 664*c*, the attachment state of the stopper 6*b* and the detachment state of the stopper 6*b* are switched. Specifically, the stopper 6*b* is detached from the adaptor 6*a*, by resiliently deforming the pair of resiliently deformable portions 664*b* toward the center axis C1 along the circumferential direction D (see FIG. 13) about the center axis C2 (see FIG. 14) of the stopper body 64 parallel to the longitudinal direction of the surgical instrument 4. To the contrary, the stopper 6*b* is attached to the adaptor 6*a* from the detached state, by resiliently deforming the pair of resiliently deformable portions 664*b* away from the center axis C1 along the circumferential direction D (see FIG. 13) about the center axis C2 (see FIG. 14) of the stopper body 64 parallel to the longitudinal direction of the surgical instrument 4. In the attached state of the stopper 6*b*, the pair of guide rails 62 of the adaptor 6*a* is sandwiched between the pair of engagement portions 664*a* of the attachment portion 664 in the X direction.

(Rotation Restriction Portion)

Figure 14:
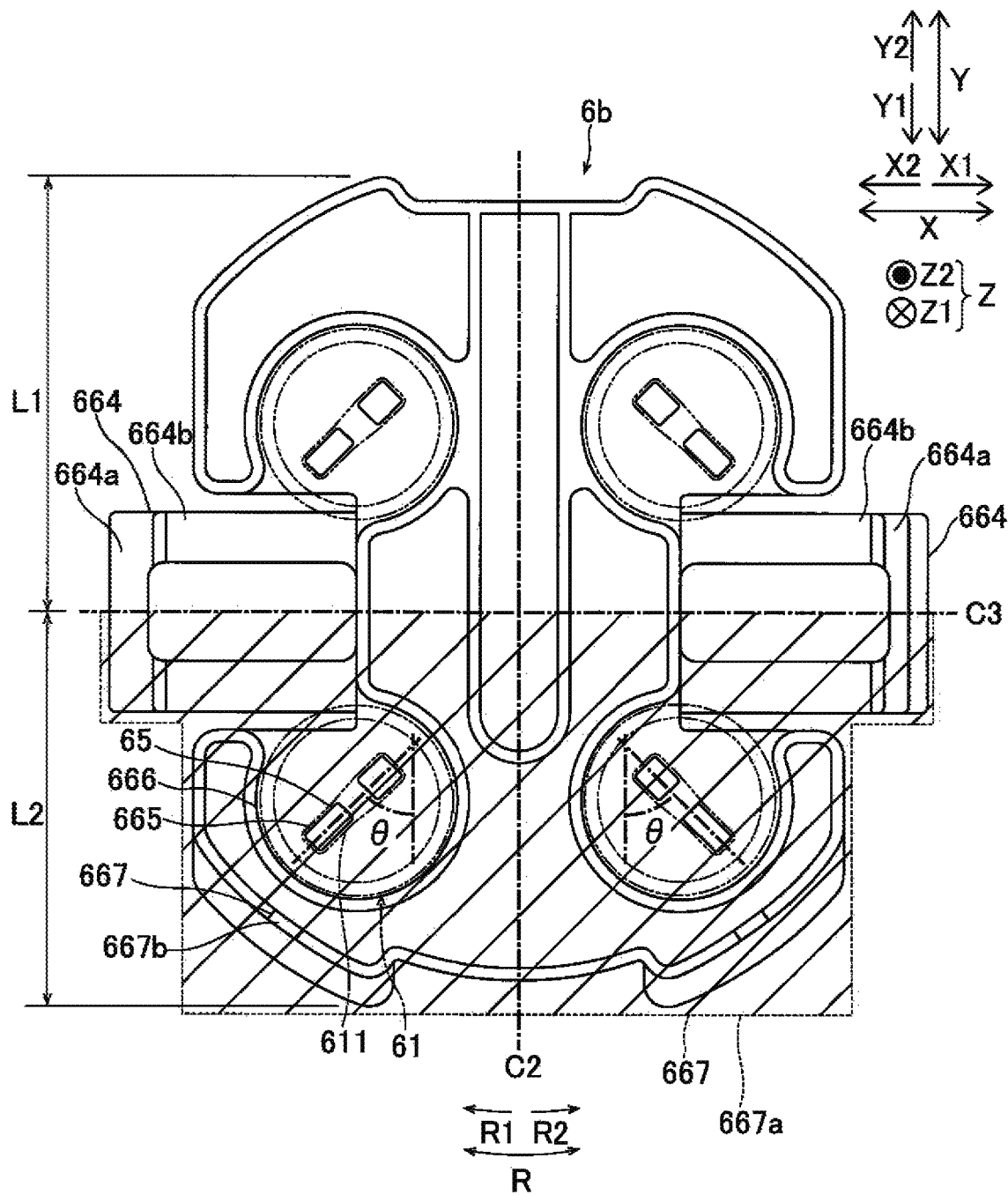
FIG. 14 is a diagram illustrating a plan view of the stopper according to a first embodiment as viewed from the Z2 side.

As illustrated in FIGS. 13 and 14, each rotation restriction portion 65 is configured to restrict the rotations of the corresponding drive transmission member 61, with making the drive transmission member 61 inclined by a predetermined angle θ, with respect to the center axis C2 of the stopper body 64 parallel to the longitudinal direction (the Y direction) of the surgical instrument 4, in the circumferential direction R about the rotational axis C1 of the drive transmission member 61.

Note that one side along the circumferential direction R is referred to as a first circumferential direction R1 and the other side along the circumferential direction R is referred to as a second circumferential direction R2.

Specifically, the rotation restriction portion 65 is configured to fix an initial position (initial state) of the engagement recess 611 of the corresponding drive transmission member 61 in the adaptor 6*a* to a position inclined by the predetermined angle θ, to prevent the engagement projection 441 (see FIG. 5) of the surgical instrument 4 from being placed on the edge of the engagement recess 611 of the drive transmission member 61 of the adaptor 6*a* when attaching the surgical instrument 4 to the adaptor 6*a*. Note that the initial state refers to a state at the start of the operation of engaging the engagement projection 441 of the surgical instrument 4 with the corresponding engagement recess 611 of the adaptor 6*a* when attaching the surgical instrument 4 to the adaptor 6*a*.

The predetermined angle θ is an angle by which the engagement projection 441 (see FIG. 5) of the surgical instrument 4 is not completely engaged with the corresponding engagement recess 611 of the adaptor 6*a* in the initial state. The predetermined angle θ is set to the same as a later-described second initial angle $θ_2$. In a first embodiment, the predetermined angle θ may be 5 degrees or more and 80 degrees or less in either the first circumferential direction R1 or the second circumferential direction R2 with respect to the center axis C2, for example. Note that it may be preferable that the predetermined angle θ is inclined with respect to the center axis C2 at 45 degrees in either the first circumferential direction R1 or the second circumferential direction R2, from the viewpoint of the time required to engage the engagement projection 441 of the surgical instrument 4 with the engagement recess 611 of the adaptor 6*a* and the assuredness of the engagement between the engagement projection 441 of the surgical instrument 4 and the engagement recess 611 of the adaptor 6*a*.

The rotation restriction portion 65 is configured to be in contact with an inside surface of the engagement recess 611 of the adaptor 6*a*, to thereby restricting the rotations of the drive transmission member 61 with the drive transmission member 61 inclined with respect to the center axis C2, to either the first circumferential direction R1 or the second circumferential direction R2 about the center axis C1 of the stopper body 64, by the predetermined angle θ.

Specifically, the rotation restriction portion 65 includes a fitting projection 665 fitted to the engagement recess 611 of the adaptor 6*a*, which is recessed from the surgical instrument 4 side surface of the drive transmission member 61 in the direction away from the surgical instrument 4. The fitting projection 665 is provided at the stopper body 64 with being inclined by the predetermined angle θ.

The fitting projection 665 is provided at the Z2 side surface of the stopper body 64. The fitting projection 665 has a block shape (substantially rectangular parallelepiped shape). The fitting projection 665 is projected from the Z2 side surface of the stopper body 64 toward the Z2 side. The fitting projection 665 has a projecting length (height) accommodated within the thickness of the stopper body 64. The fitting projection 665 is divided in plural (two) pieces arranged in the direction inclined at the predetermined angle θ with respect to the center axis C2.

The fitting projection 665 extends in a direction inclined by the predetermined angle θ to either the first circumferential direction R1 or the second circumferential direction R2 with respect to the center axis C2. That is, the fitting projection 665 is relatively inclined by the predetermined angle θ to either the first circumferential direction R1 or the second circumferential direction R2 with respect to the engagement recess 611 of the adaptor 6*a*.

By manually rotating the drive transmission member 61 (the engagement recess 611) of the adaptor 6*a* by the worker, the fitting projection 665 of the stopper 6*b* gets fitted to the engagement recess 611 of the drive transmission member 61 of the adaptor 6*a*. Here, the fitting projection 665 is fitted to the engagement recess 611 of the adaptor 6*a* with a small gap therebetween (i.e., a loose fit state).

In the state where the fitting projection 665 of the stopper 6*b* and the engagement recess 611 of the adaptor 6*a* are fitted to each other, the fitting projection 665 is in contact with the inner surface of the engagement recess 611 of the adaptor 6*a*, to thereby restricting the rotations of the engagement recess 611 of the adaptor 6*a* due to the rotations of the engagement projection 211 of the drive part 21*b*. Further, in the state where the fitting projection 665 of the stopper 6*b* and the engagement recess 611 of the adaptor 6*a* are fitted to each other, the fitting projection 665 is in contact with the inner surface of the engagement recess 611 of the adaptor 6*a*, to thereby restricting relative movements of the stopper body 64 with respect to the adaptor 6*a* in the X direction and the Y direction.

In a case where the adaptor 6*a* includes plural (four) engagement recesses 611 on the surgical instrument 4 side surface 63 thereof, the stopper body 64 includes plural (four) fitting projections 665, to correspond to the number of the plural engagement recesses 611 of the adaptor 6*a*.

The fitting projections 665 are provided on a surface of the stopper body 64 opposed to the surgical instrument 4 side surface 63 of the adaptor 6a. Each of the fitting projections 665 is located at the position where the fitting projection 665 can be surely fitted to the corresponding engagement recess 611 of the adaptor 6a by manually rotating the engagement recesses 611 of the adaptor 6a by the worker.

The plural fitting projections 665 are provided at the stopper body 64 with being inclined at the predetermined angle θ in such a manner that the plural fitting projections 665 are line-symmetrically arranged with respect to the center axis C2 of the stopper body 64 parallel to the longitudinal direction of the surgical instrument 4.

For example, the number of the fitting projections 665 provided on the X1 side with respect to the center axis C2 of the stopper body 64 and the number of the fitting projections 665 provided on the X2 side with respect to the center axis C2 of the stopper body 64 are the same (two). Two of the fitting projections 665 are provided on the X1 side of the center axis C2 of the stopper body 64 and arranged side by side in the Y direction with being inclined with respect to the center axis C2 toward the second circumferential direction R2 by the predetermined angle θ. To the contrary, the other two of the fitting projections 665 are provided on the X2 side of the center axis C2 of the stopper body 64 and arranged side by side in the Y direction with being inclined with respect to the center axis C2 toward the first circumferential direction R1 by the predetermined angle θ.

(Restriction Portion Recess)

The rotation restriction portion 65 is configured to have the structure that suppresses the thickness, in the Z direction, of portions of the stopper body 64 in the vicinity of the fitting projections 665.

Specifically, the rotation restriction portion 65 includes a restriction portion recess 666 provided around the fitting projection 665 and recessed toward the direction (the Z1 direction) away from the adaptor 6. The restriction portion recess 666 is configured such that the outer circumferential portion of the drive transmission member 61 is inserted into the restriction portion recess 666.

Specifically, by inserting the fitting projection 665 into the engagement recess 611 of the adaptor 6a up to the base portion of the fitting projection 665 on the Z1 side in the state where the fitting projection 665 of the stopper 6b and the engagement recess 611 of the adaptor 6a are fitted to each other, the outer circumferential portion of the drive transmission member 61 is inserted into the restriction portion recess 666. The restriction portion recess 666 is recessed from the Z2 side surface of the stopper body 64 toward the Z1 side along the Z direction. In the Z direction, the length of the restriction portion recess 666 is larger than the projecting length of the fitting projection 665. In the Z direction, the length of the restriction portion recess 666 is smaller than the maximum thickness of the stopper body 64. Note that the outer circumferential portion of the drive transmission member 61 is a portion of the Z1 side portion of the drive transmission member 61 other than the engagement recess 611 of the adaptor 6a.

As viewed from the Z2 side, the shape of the restriction portion recess 666 corresponds to the shape of the drive transmission member 61. Here, as viewed from the Z2 side, the inner diameter of the restriction portion recess 666 is larger than the drive transmission member 61.

(Discrimination Portion)

The stopper body 64 is configured such that the worker can recognize the correct orientation of the stopper 6b with respect to the adaptor 6a, upon attaching the stopper 6b to the adaptor 6a.

Specifically, the stopper body 64 includes a discrimination portion 667 to indicate (discriminate) the orientation of the stopper 6b with respect to the longitudinal direction of the surgical instrument 4 upon attaching the stopper 6b to the adaptor 6a (see FIG. 4).

The discrimination portion 667 includes a first discrimination portion 667a and a second discrimination portion 667b.

The first discrimination portion 667a is configured such that one side of the stopper body 64 is smaller than the other side of the stopper body 64 in the longitudinal direction of the surgical instrument 4 (the Y direction). That is, the first discrimination portion 667a is configured such that a length L2 (see FIG. 14) of a portion of the stopper body 64 on the Y1 side with respect to the center line C3 of the grab portions 664c extending in the X direction is smaller than a length L1 (see FIG. 14) of a portion of the stopper body 64 on the Y2 side with respect to the center line C3.

The second discrimination portion 667b is configured to have a recess 667c or a cutout at only one side, in the longitudinal direction of the surgical instrument 4 (the Y direction), of a rim (or an edge) of the stopper body 64. That is, the second discrimination portion 667b is configured to have the recess 667c such that the recess 667c (cutout) is formed at the rim or the edge of the stopper body 64 only on the Y1 side with respect to the center line C3 of the grab portions 664c, but not formed on the Y2 side with respect to the center line C3, in the longitudinal direction of the surgical instrument 4 (the Y direction). Here, the recess 667c is recessed from the end of the rim of the stopper body 64 on the Z2 side toward the Z1 side.

(Method of Assembling Adaptor)

Figure 16:
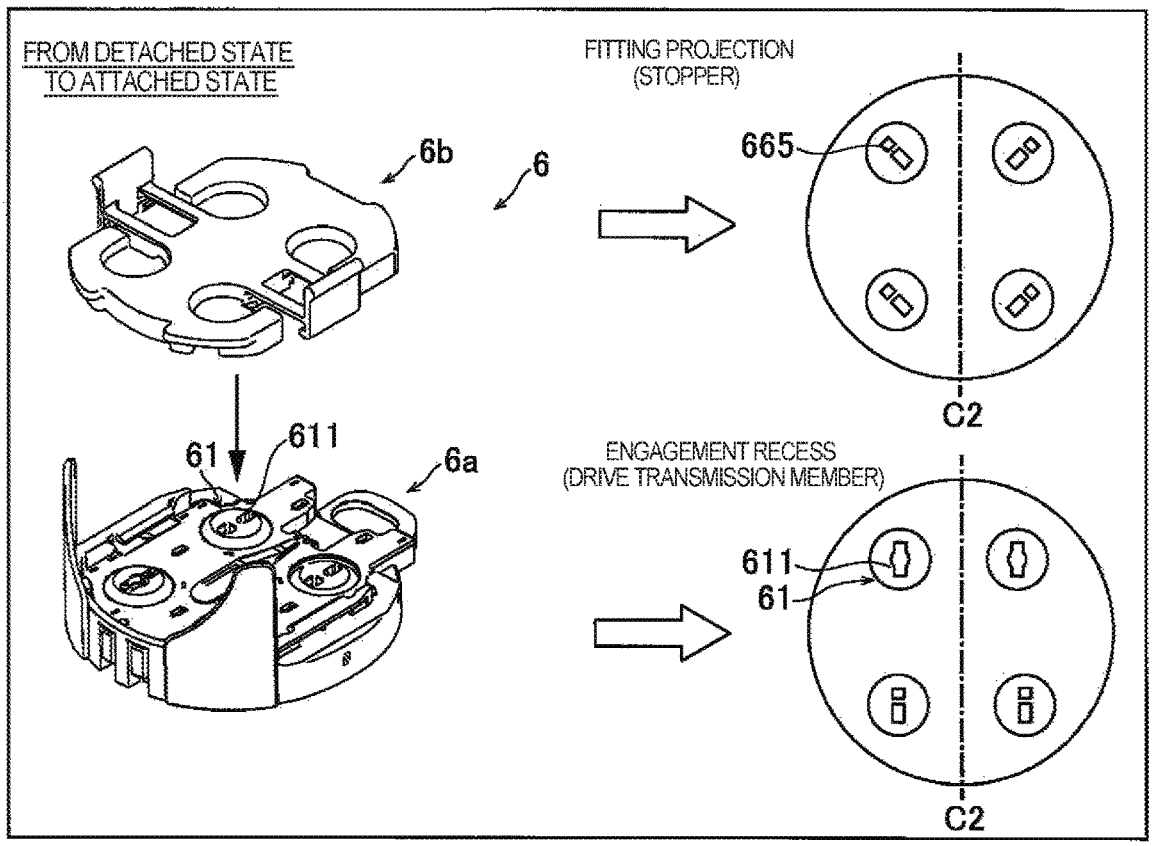
FIG. 16 is diagram illustrating a schematic view of a state when the stopper is attached to the drive transmission members according to a first embodiment.
Figure 17:
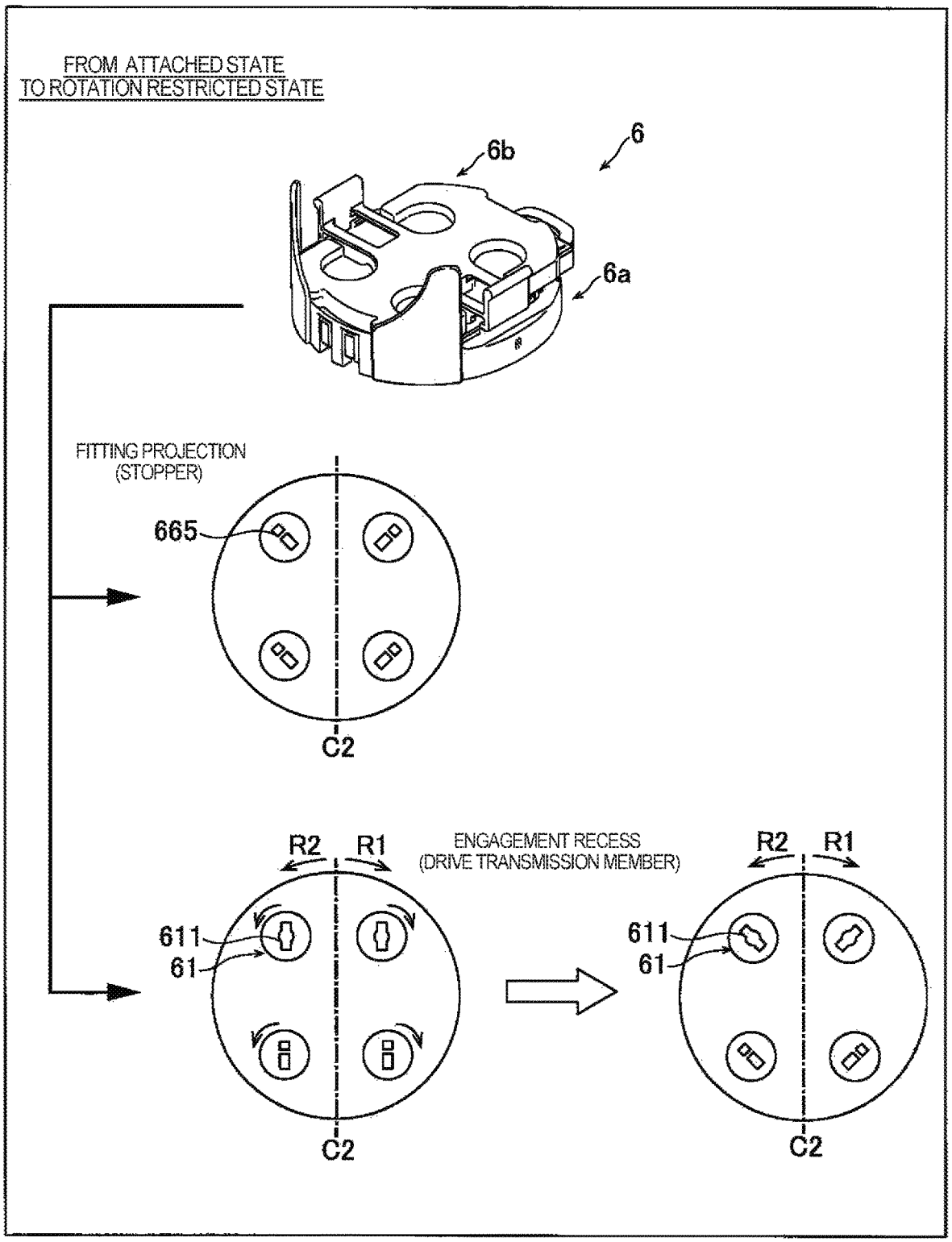
FIG. 17 is a diagram illustrating a schematic view of a state in which rotations of the drive transmission members are regulated by the stopper according to a first embodiment.

Hereinafter, with reference to FIGS. 15 to 17, a method of assembling the stopper-attached adaptor 6, which includes the adaptor 6a and the stopper 6b. Note that an adaptor manufacturer assembles the stopper-attached adaptor 6. By this assembling method, the stopper-attached adaptor 6 is set up which is capable of retaining a state in which the inclination angles of the engagement recesses 611 of the adaptor 6a are fixed and retained at the predetermined angle θ. Note that in FIGS. 16 and 17, the center axis C2 of the stopper body 64 is illustrated to the adaptor 6a and the first circumferential direction R1 and the second circumferential direction R2 are illustrated to the adaptor 6a, to facilitate understanding.

Figure 15:
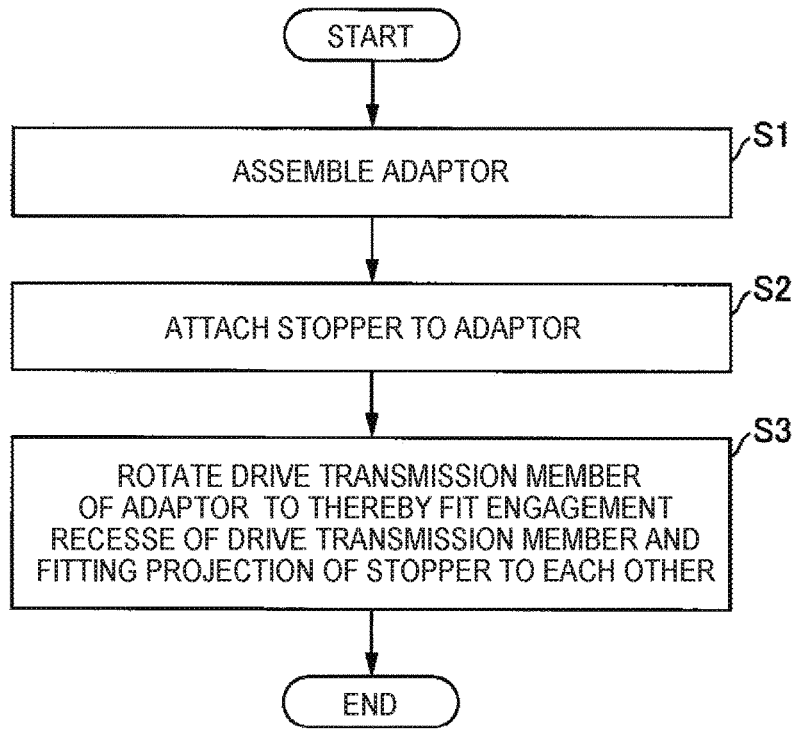
FIG. 15 is a flowchart illustrating a method of assembling a stopper-attached adaptor according to a first embodiment.

As illustrated in FIG. 15, in Step S1, the worker assembles the adaptor 6a.

In Step S2, the worker attaches the stopper 6b to the adaptor 6a. Specifically, as illustrated in FIG. 16, the worker puts the detached stopper 6b closer to the adaptor 6a, and then attaches the stopper 6b to the adaptor 6a in a state where the fitting projections 665 of the stopper 6b and the drive transmission members 61 of the adaptor 6a are in contact with each other. As a result, the pair of engagement portions 664a of the stopper 6b and the pair of guide rails 62 of the adaptor 6a are respectively engaged with each other. In this state, the fitting projections 665 of the stopper 6b are inclined with respect to the direction of the center axis C2 by the predetermined angle θ, while the engagement recesses 611 of the adaptor 6a are substantially parallel to the direction of the center axis C2. Note that, in this state, it is not limited to the case where the engagement recesses 611 of the adaptor 6a are substantially parallel to the direction of the center axis C2, but the engagement recesses 611 of the adaptor 6a may be inclined with respect to the direction of the center axis C2 by an angle(s) different from the predetermined angle θ, for example.

As illustrated in FIG. 15, in Step S3, the worker rotates the drive transmission members 61 of the adaptor 6a to thereby fit the engagement recesses 611 of the adaptor 6a and the fitting projections 66 of the stopper 6b to each other. Specifically, as illustrated in FIG. 17, the worker rotates the drive transmission members 61 of the adaptor 6a manually (for example, operating directly by hand or using a tool) in the state where the stopper 6b is attached to the adaptor 6a, to thereby fit the engagement recesses 611 of the adaptor 6a and the fitting projections 665 of the stopper 6b to each other. At this time, the worker rotates, in the first circumferential direction R1, the engagement recesses 611 provided on one side from the center axis C2 among all the engagement recesses 611 of the adaptor 6a, whereas the worker rotates, in the second circumferential direction R2, the engagement recesses 611 provided on the other side from the center axis C2 among all the engagement recesses 611 of the adaptor 6a.

With this assembling method, the stopper-attached adaptor 6 that can fix and hold the engagement recesses 611 of the adaptor 6a at the positions inclined by the predetermined angle θ is manufactured. Then, the operation of assembling the stopper-attached adaptor 6 by the worker is ended. Note that a package in which the stopper-attached adaptor 6 and the drape 7 (see FIG. 4) are packed together is shipped as a product.

(Method of Fixing Surgical Instrument to Robot Arm)

Figure 19:
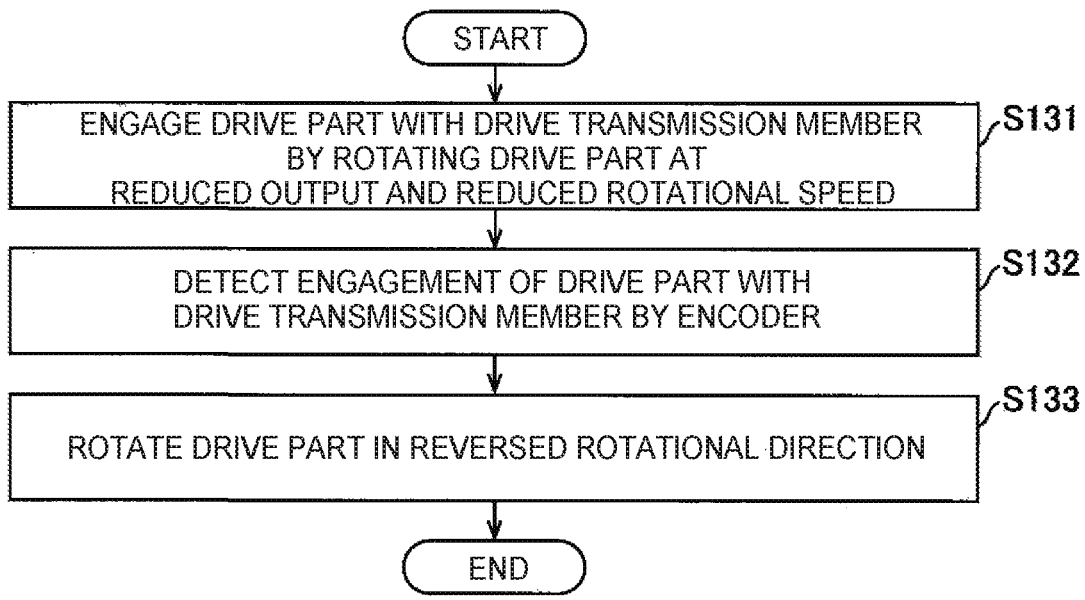
FIG. 19 is a flowchart illustrating a method of engaging the drive part with the drive transmission member according to a first embodiment.
Figure 20:
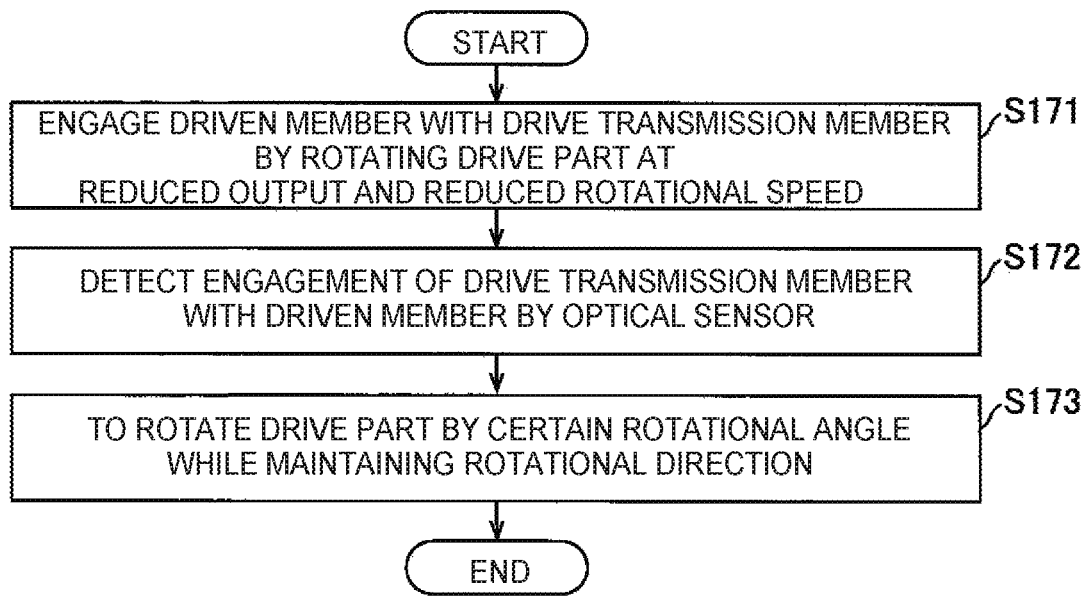
FIG. 20 is a flowchart illustrating a method of engaging the drive transmission member with the driven member according to a first embodiment.
Figure 21:
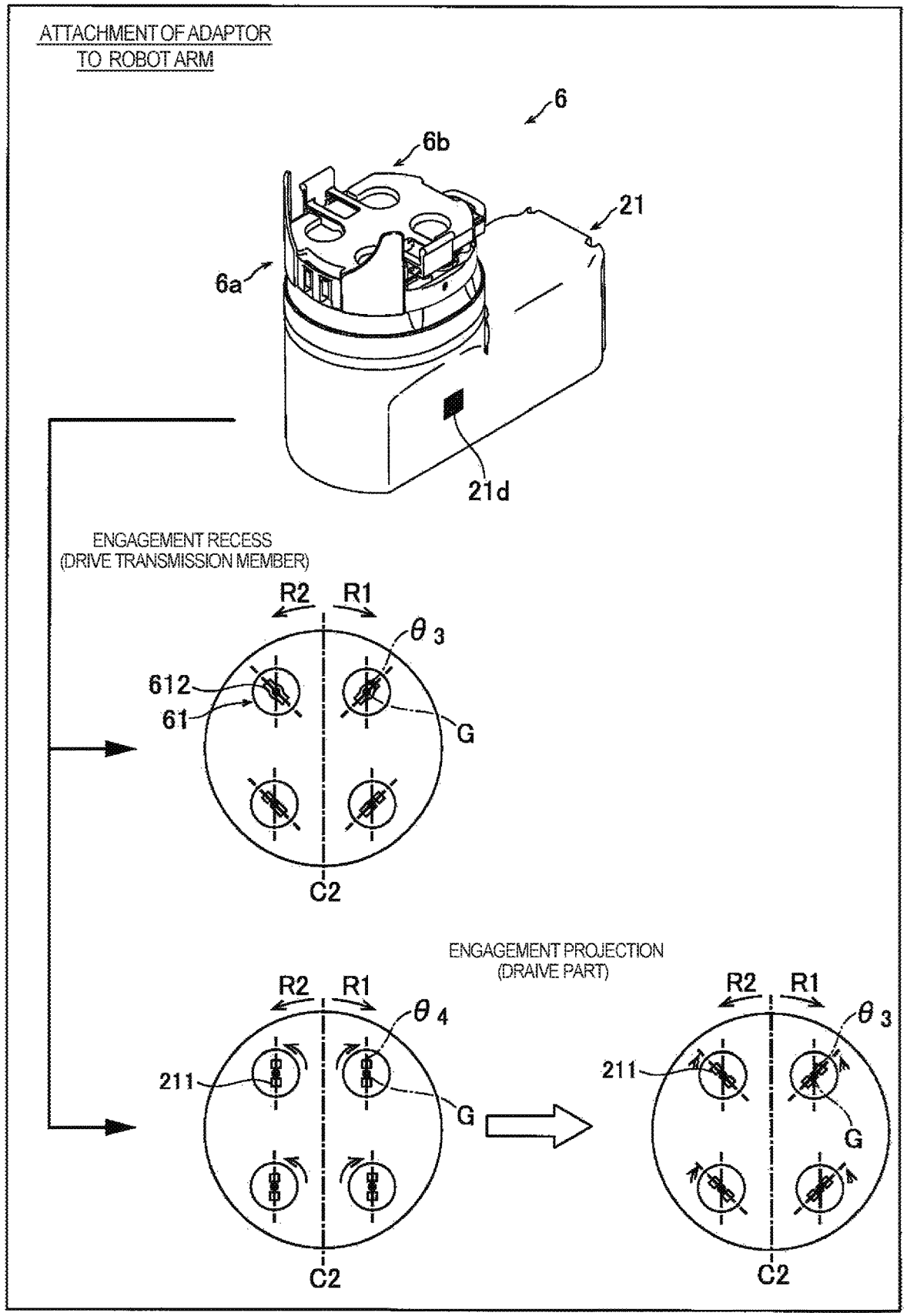
FIG. 21 is a diagram illustrating a schematic view of a state when the adaptor is attached to the robot arm according to a first embodiment.
Figure 22:
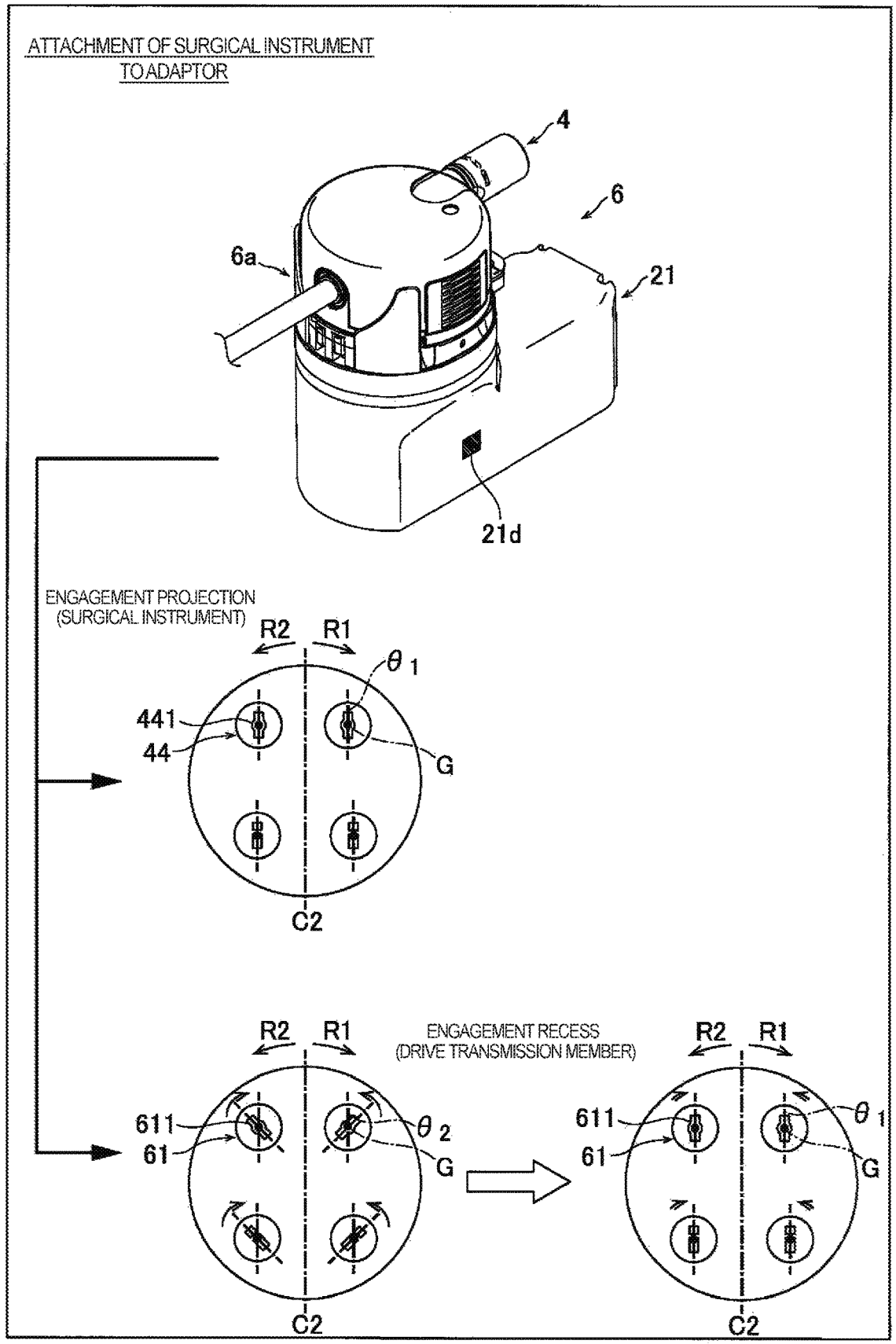
FIG. 22 is a diagram illustrating a schematic view of a state when the surgical instrument is attached to the adaptor according to a first embodiment.

With reference to FIGS. 18 to 22, a method of fixing the surgical instrument 4 to the robot arm 21 is described below. The method of fixing the surgical instrument 4 to the robot arm 21 is a method of fixing the surgical instrument 4 to the drive parts 21b of the robot arm 21 via the adaptor 6a The process of fixing the surgical instrument 4 to the robot arm 21 via the adaptor 6a may be executed by an assistant Sp (see FIG. 1) as a worker of the user. In FIGS. 21 and 22, the center axis C2 and the center axis G are illustrated to the adaptor 6a, the drive parts 21b, and the surgical instrument 4 to facilitate understanding and the first circumferential direction R1 and the second circumferential direction R2 are also illustrated to the adaptor 6a, the drive parts 21b, and the surgical instrument 4 to facilitate understanding.

Figure 18:
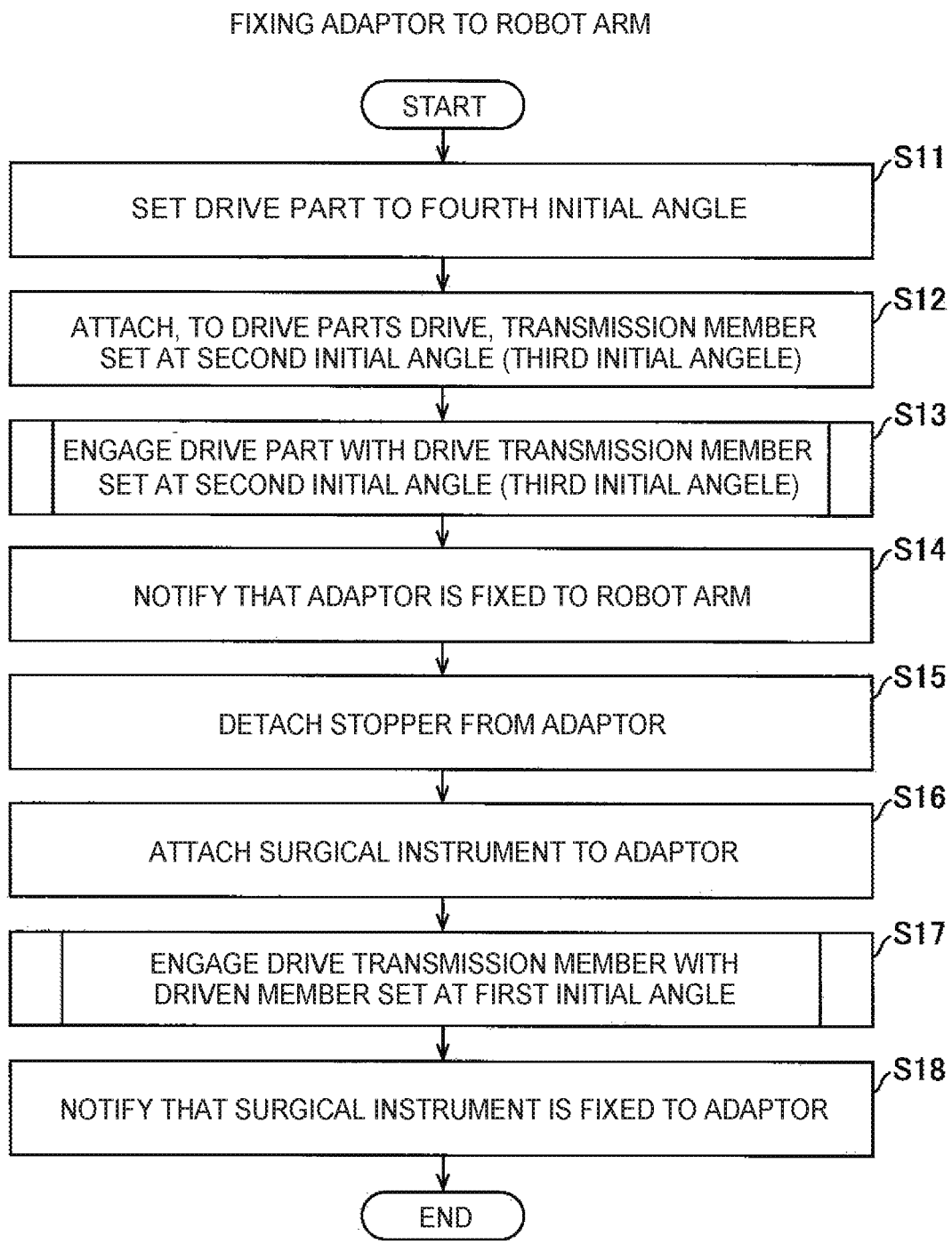
FIG. 18 is a flowchart illustrating a method of fixing the surgical instrument to the robot arm using the stopper according to a first embodiment.

As illustrated in FIGS. 18 and 21, the method of fixing the surgical instrument 4 to the robot arm 21 include attaching the adaptor 6a to the robot arm 21, and then rotating the drive parts 21b of the robot arm 21 to thereby engage the engagement projections 211 of the drive parts 21b to the engagement recesses 612 of the drive transmission members 61 of the adaptor 6a at a third initial angle $\theta_3$ (predetermined angle θ). The third initial angle $\theta_3$ is an angle between the center axis C2 and the center line of the engagement recess 612 along the longitudinal direction of the engagement recess 612 (the direction in which the engagement recess 612 extends). Note that the third initial angle $\theta_3$ is an example of a third initial orientation.

In a first embodiment, the third initial angle $\theta_3$ is set to an angle same as a later described second initial angle $\theta_2$ of the engagement recesses 611. With this, the second initial angle $\theta_2$ of the engagement recesses 611 of the drive transmission members 61 and the third initial angle $\theta_3$ of the engagement recesses 612 of the drive transmission members 61 can be more easily set to desire initial angles, than a case where the second initial angle $\theta_2$ of the engagement recesses 611 of the drive transmission members 61 and the third initial angle $\theta_3$ of the engagement recesses 612 of the drive transmission members 61 are different from each other. However, in a modification, the third initial angle $\theta_3$ and the second initial angle $\theta_2$ may be different.

Specifically, the method of fixing the surgical instrument 4 to the robot arm 21 includes Step 11 to set (rotate) the engagement projections 211 of the drive parts 21b to a fourth initial angle $\theta_4$. In Step S11, the engagement projections 211 of the drive parts 21b are set to the fourth initial angle $\theta_4$, which does not correspond to the third initial angle $\theta_3$ of the engagement recesses 612 of the drive transmission members 61. That is, the engagement projections 211 of the drive parts 21b is set to the fourth initial angle $\theta_4$ different from the third initial angle $\theta_3$ so as not to be engaged with the engagement recesses 612 of the drive transmission members 61 set at the third initial angle $\theta_3$. The fourth initial angle $\theta_4$ is an angle between the center axis C2 and the center line of the engagement projection 211 along the longitudinal direction of the engagement projection 211 of the drive part 21b (the direction in which the projected portions of the engagement projection 211 are arranged). Note that the fourth initial angle $\theta_4$ is an example of a fourth initial orientation.

As described above, the fourth initial angle $\theta_4$ is different from the third initial angle $\theta_3$. That is, the center line along the longitudinal direction of the engagement projection 211 of each of the drive parts 21b is inclined with respect to the center line along the longitudinal direction of the engagement recess 612 of each of the drive transmission members 61 set at the third initial angle $\theta_3$. It may be preferable that the fourth initial angle $\theta_4$ is inclined by not less than 5 degrees and not more than 80 degrees with respect to the third initial angle $\theta_3$. Note that in terms of the time required for and the certainty of the engagement between the engagement recesses 612 of the adaptor 6a and the engagement projections 211 of the drive parts 21b, it may be further preferable that the fourth initial angle $\theta_4$ is inclined by 45 degrees with respect to the third initial angle $\theta_3$. In a first embodiment, the third initial angle $\theta_3$ is set to 45 degrees and the fourth initial angle $\theta_4$ is set to 0 degree with respect to the center axis C2. Note that the above described degrees of the third initial angle $\theta_3$ and the fourth initial angle $\theta_4$ are only examples and thus the disclosure is not limited to these.

The method of fixing the surgical instrument 4 to the robot arm 21 includes Step S12 in which the worker (the assistant Sp (see FIG. 1)) attaches, to the drive parts 21b of the robot arm 21, the stopper-attached adaptor 6 in which the engagement recesses 611 of the drive transmission members 61 are preset to the second initial angle $\theta_2$ and the engagement recesses 612 of the drive transmission members 61 are preset to the third initial angle $\theta_3$. The second initial angle $\theta_2$ is set to be different from a first initial angle $\theta_1$ so as not to engage the engagement recesses 611 set in the second initial angle $\theta_2$ to the engagement projections 441 of the driven members 44 of the surgical instrument 4 set in the first initial angle $\theta_1$. That is, the engagement recesses 611 of the drive transmission members 61 are set to the second initial angle $\theta_2$, wherein the second initial angle $\theta_2$ does not correspond to the first initial angle $\theta_1$ to which the engagement projections 441 of the driven members 44 are set. Note that the first initial angle $\theta_1$ is an angle between the center axis C2 and the center line of the engagement projection 441 along the longitudinal direction of the engagement projection 441 of the driven member 44, and the second initial angle $\theta_2$ is an angle between the center axis C2 and the center line along the longitudinal direction of the engagement recess 611 of the drive transmission member 61. Accordingly, the center line along the longitudinal direction of the engagement projection 441 (the direction in which the projected portions of the engagement projection 441 are arranged) is inclined with respect to the center line along the longitudinal direction of the engagement recess 611 of the drive transmission member 61 set at the second initial angle $\theta_2$. It may be preferable that the second initial angle $\theta_2$ is inclined by not less than 5 degrees and not more than 80 degrees with respect to the first initial angle $\theta_1$. Note that in terms of the time required for and the certainty of the engagement between the engagement recesses 611 of the adaptor 6a and the engagement projections 441 of the driven members 44, it may be further preferable that the first initial angle $\theta_1$ is inclined by 45 degrees with respect to the second initial angle $\theta_2$. In a first embodiment, the first initial angle $\theta_1$ is set to 0 degree and the second initial angle $\theta_2$ is set to 45 degrees with respect to the center axis C2. The above described degrees of the first initial angle $\theta_1$ and the second initial angle $\theta_2$ are only examples and thus the disclosure is not limited to these. Note that the first initial angle $\theta_1$ is an example of a first initial orientation and the second initial angle $\theta_2$ is an example of a second initial orientation. As described above, the worker attaches the adaptor 6a to which the stopper 6b is attached, to the robot arm 21.

The method of fixing the surgical instrument 4 to the robot arm 21 includes Step S13 to engage the engagement projections 211 of the drive parts 21b to the engagement recesses 612 of the drive transmission members 61 set at the third initial angle $\theta_3$. That is, in Step S13 after the adaptor 6a is attached to the drive parts 21b of the robot arm 21, the drive parts 21b are rotated to engage the engagement projections 211 with the engagement recesses 612 set at the third initial angle $\theta_3$.

As described above, in Step 3 in the assembling the stopper-attached adaptor 6, the engagement recesses 611 of the drive transmission members 61, which are to be engaged with the engagement projections 211 of the drive parts 21b, are preset to the second initial angle $\theta_2$ (a predetermined angle $\theta$), the engagement recesses 612 of the drive transmission members 61 are preset to the third initial angle $\theta_3$ (the predetermined angle $\theta$ in a first embodiment). In Step S11 in the method of fixing the surgical instrument 4 to the robot arm 21, the engagement projections 211 of the drive parts 21b are set to the fourth initial angle $\theta_4$, which does not correspond to the engagement recesses 612 of the drive transmission members 61. In Step S13 in the method of fixing the surgical instrument 4 to the robot arm 21, after the adaptor 6a is attached to the drive parts 21b of the robot arm 21, the drive parts 21b are rotated to engage the engagement projections 211 of the drive parts 21b with the engagement recesses 612 of the drive transmission members 61 set at the third initial angle $\theta_3$. That is, before the operation of engaging the engagement recesses 612 of the drive transmission members 61 with the engagement projections 211 of the drive parts 21b, the engagement projections 211 of the drive parts 21b are preset to the fourth initial angle $\theta_4$, which does not correspond to the third initial angle $\theta_3$ at which the engagement recesses 612 of the drive transmission members 61 are set. Accordingly, the initial positions of the engagement recesses 612 of the drive transmission members 61 and the initial positions of the engagement projections 211 of the drive parts 21b are not arranged to be too close to each other, so that the engagement recesses 612 and the engagement projections 211 are not unintentionally engaged with each other in an incomplete engagement manner. This can prevent the detection of the completion of the engagement between the engagement recesses 612 of the drive transmission members 61 and the engagement projections 211 of the drive parts 21b in a state where the engagement recesses 612 and the engagement projections 211 are incompletely engaged, and can ensure a sufficient rotation angle for rotating the drive parts 21b. As a result, the drive parts 21b of the robot arm 21 and the drive transmission members 61 of the adaptor 6a can be engaged with each other in a secured and substantially completed state, and the surgical instrument 4 and the adaptor 6a can be engaged with each other in a secured and substantially completed state.

As illustrated in FIGS. 19 and 21, in Step S13 in the method of fixing the surgical instrument 4 to the robot arm 21, when the controller 141 determines, based on the detection result of the encoder 215, that the engagement projections 211 of the drive parts 21b are engaged with the engagement recesses 612 of the drive transmission members 61 set to the third initial angle $\theta_3$ by rotating the drive parts 21b, the controller 141 reverses the rotational direction of the drive parts 21b to rotate the drive parts 21b in the reversed rotational direction. Note that the method of fixing the surgical instrument 4 to the robot arm 21 may not include Step S133 to rotate the drive parts 21b in the reverse rotational direction.

Step S13, which is a step of engaging the drive parts 21b and the drive transmission members 61 with each other, includes Step S131 to rotate the drive parts 21b at a reduced output (torque) and a reduced rotational speed, to thereby engage the engagement projections 211 of the drive parts 21b with the engagement recesses 612 of the drive transmission members 61. That is, in Step S131, the drive parts 21b are driven at the reduced output and the reduced rotational speed lower than a normal output and a normal rotational speed of the drive parts 21b when performing the surgery.

Specifically, in Step S131, the drive parts 21b are engaged with the drive transmission members 61, by rotating the engagement projections 211 of the drive parts 21b with the reduced output of the drive parts 21b lower than the normal output of the drive parts 21b when performing the surgery with the surgical instrument 4. That is, in Step S131, the drive parts 21b are rotated with whose torques being suppressed.

Further, in Step S131, the drive parts 21b are engaged with the drive transmission members 61, by rotating the engagement projections 211 of the drive parts 21b with the reduced rotational speed of the drive parts 21b slower than the normal rotational speed of the drive parts 21b when performing the surgery with the surgical instrument 4. That is, in Step S131, the drive parts 21b are rotated with whose rotational speed being suppressed.

Step S13, which is the step of engaging the drive parts 21b and the drive transmission members 61 with each other, further includes Step S132 to detect the engagement of the drive parts 21b with the drive transmission members 61 by the encoder 215. That is, in Step S132, when the rotation speed of the drive parts 21b falls below the threshold, the engagement between the engagement projections 211 of the drive parts 21b and the engagement recesses 612 of the drive transmission members 61 is detected.

Step S13, which is the step of engaging the drive parts 21b and the drive transmission members 61 with each other, further includes Step S133 to reverse the rotational direction of the drive parts 21b.

That is, in Step S132, the engagement of the engagement projections 211 of the drive parts 21b with the engagement recesses 612 of the drive transmission members 61 is detected by the encoder 215. In Step S133, after the engagement of the engagement projections 211 of the drive parts 21b with the engagement recesses 612 of the drive transmission members 61 is detected, the drive parts 21b are rotated in the reverse rotational direction (a second rotational direction) opposite to the rotational direction (a first rotational direction) of the drive parts 21b before detecting the engagement of the engagement projections 211 of the drive parts 21b with the engagement recesses 612 of the drive transmission members 61. Accordingly, even if the engagement projections 211 of the drive parts 21b passes the target rotational position at which the engagement projections 211 of the drive parts 21b and the engagement recesses 612 of the drive transmission members 61 are engaged with each other, and thus the engagement between the engagement recesses 612 of the drive transmission members 61 and the engagement projections 211 of the drive parts 21b is detected based on an decrease on the rotational speed of the engagement projections 211 of the drive parts 21b due to the engagement recesses 612 of the drive transmission members 61 suppressing the rotations of the engagement projections 211 of the drive parts 21b, the reversed rotation of the drive parts 21b in Step 13 can decrease an amount of a misalignment therebetween. Therefore, the engagement recesses 612 of the drive transmission members 61 and the engagement projections 211 of the drive parts 21b can be more reliably engaged with each other.

The method of fixing the surgical instrument 4 to the robot arm 21 includes Step S14 to notify that the adaptor 6a is fixed to the robot arm 21. That is, in Step S14, the completion of fixing the adaptor 6a to the robot arm 21 is notified in response to the detection of the engagement between the drive transmission members 61 and the drive parts 21b. Specifically, in Step S14, the completion of fixing the adaptor 6a to the robot arm 21 is notified to the worker by the lamp 21d.

The method of fixing the surgical instrument 4 to the robot arm 21 includes Step S15 in which the worker detaches the stopper 6b from the adaptor 6a. In Step S15, after the step of notifying the completion of fixing of the adaptor 6a to the robot arm 21, the worker detaches the stopper 6b from the adaptor 6a.

The method of fixing the surgical instrument 4 to the robot arm 21 includes Step S16 in which the worker attaches the surgical instrument 4 to the adaptor 6a.

As described above, in Step S12, the adaptor 6a having the stopper 6b attached thereto is attached to the robot arm 21, with the stopper 6b fixing the engagement recesses 611 of the drive transmission members 61 of the adaptor 6a at the second initial angle $\theta_2$ and the engagement recesses 612 of the drive transmission members 61 of the adaptor 6a at the third initial angle $\theta_3$. Then, in Step S15, after the engagement projections 211 of the drive parts 21b and the engagement recesses 612 of the drive transmission members 61 are engaged with each other, the stopper 6b is detached from the adaptor 6a. Then, in Step S16, after the stopper 6b is detached from the adaptor 6a, the surgical instrument 4 is attached to the adaptor 6a. Accordingly, since the stopper 6b can securely retain the engagement recesses 612 of the drive transmission members 61 to the third initial angle $\theta_3$, the initial positions of the engagement recesses 612 of the drive transmission members 61 (second engagement portions of drive transmission members) and the initial positions of the engagement projections 211 of the drive parts 21b (engagement portions of drive parts) are not relatively arranged to be too close to each other so that the engagement recesses 612 are not unintentionally engaged with the engagement projections 211 in an incomplete engagement manner, and thus a sufficient rotation angle for rotating the drive parts 21b can be ensured. Further, the stopper 6b, which has been detached from the adaptor 6a upon attaching the surgical instrument 4 to the adaptor 6a, restricts the rotations of the drive transmission members 61. Accordingly, the adaptor 6a itself does not need to have a structure for regulating the rotations of the drive transmission members 61. Therefore, without providing an extra internal structure and/or an extra internal space in the adaptor 6a, the rotations of the drive transmission members 61 can be restricted, and the drive parts 21b and the drive transmission members 61 can be engaged with each other in the secured and substantially completed state.

As illustrated in FIGS. 18 and 22, the method of fixing the surgical instrument 4 to the robot arm 21 includes Step S17 to engage the drive transmission members 61 with the driven members 44 set at the first initial angle $\theta_1$. That is, in Step S17, the drive parts 21b are rotated to engage the engagement recesses 611 of the drive transmission members 61 with the engagement projections 441 of the driven members 44.

Specifically, in Step S17 in the method of fixing the surgical instrument 4 to the robot arm 21 according to a first embodiment, the drive parts 21b are rotated to rotate the drive transmission members 61 having the engagement recesses 611 set at the second initial angle $\theta_2$, which does not correspond to the first initial angle $\theta_1$ of the engagement projections 441 of the driven members 44, to thereby engage the drive transmission members 61 to the driven members 44. In Step S17, the engagement recesses 611 of the drive transmission members 61 are engaged with the engagement projections 441 of the driven members 44. Note that, the engagement recesses 611 of the drive transmission members 61 are fixed to the second initial angle $\theta_2$ by the stopper 6b in advance, in the method of assembling the stopper-attached adaptor as illustrated in FIG. 15.

As illustrated in FIGS. 20 and 22, Step S17 includes Step S171 to rotate the drive parts 21b at a reduced output (torque) and a reduced rotational speed of the drive parts 21b, to engage the drive transmission members 61 with the driven members 44. That is, in Step S171, the drive parts 21b are driven at the reduced output and the reduced rotational speed lower than a normal output (torque) and a normal rotational speed when performing the surgery.

Specifically, in Step S171, the drive parts 21b are driven to rotate the drive transmission members 61 at the reduced output and the reduced rotational speed lower than the normal output (torque) and the normal rotational speed when performing the surgery with the surgical instrument 4, to thereby engage the drive transmission members 61 to the driven members 44. This can prevent unintentional movements of the driven members 44 when the drive transmission members 61 and the driven members 44 are engaged with each other, because of the reduced torque (rotation force) applied to the drive transmission members 61.

That is, in Step S171, the drive parts 21b are driven at the reduced torque to rotate the drive transmission members 61.

Further, in Step S171, the drive parts 21b are driven at the reduced rotational speed lower than the normal rotational speed when performing the surgery with the surgical instrument 4, to rotate the drive transmission members 61, to thereby engage the drive transmission members 61 to the driven members 44. With this, the drive transmission members 61 can be more easily engaged with the driven members 44, and thereby the surgical instrument 4 and the adaptor 6a are engaged with each other in a more secure and more complete state.

That is, in Step S171, the drive parts 21b are driven at the reduced rotational speed of the drive parts 21b to rotate the drive transmission members 61.

Step S17 further includes Step S172 to detect the engagement of the drive transmission members 61 with the driven members 44 by the optical sensor 21c. That is, in Step S172, when the light emitted from the light emission part 221 to the light reception part 222 is blocked by the light blocking part 213a of the drive part 21b, the engagement between the engagement projections 441 of the driven members 44 and the engagement recesses 611 of the drive transmission members 61 is detected. The sensor that detects the engagement between the engagement projections 441 of the driven members 44 and the engagement recesses 611 of the drive transmission members 61 is not limited to an optical sensor, but may be a sensor that detects a change in the height of the detection member due to the change of the engagement state, such as a magnetic sensor or the like, for example.

Step S17 further includes Step S173 to rotate the drive parts 21b by a predetermined rotational angle while maintaining the rotational direction. That is, in Step S173, when the controller 141 determines, based on the detection result of the optical sensor 21c, that the drive transmission members 61 are engaged with the driven members 44 by the rotation of the drive parts 21b, the controller 141 overruns the drive parts 21b by the predetermined rotational angle.

As described above, in Step S172, the engagement of the engagement recesses 611 of the drive transmission members 61 with the engagement projections 441 of the driven members 44 is detected. With this, the engagement recesses 611 of the drive transmission members 61 and the engagement projections 441 of the driven members 44 are automatically engaged with each other at the desired position. This facilitates the operation of engaging the engagement recesses 611 of the drive transmission members 61 with the engagement projections 441 of the driven members 44.

Further, in Step S172, the engagement of the engagement recesses 611 of the drive transmission members 61 with the engagement projections 441 of the driven members 44 is detected by the optical sensor 21c. With this, the engagement between the engagement projections 441 of the driven members 44 and the engagement recesses 611 of the drive transmission members 61 can be detected based on the actual position of the engagement projections 441 of the driven members 44 and the actual position of the engagement recesses 611 of the drive transmission members 61. This further improves the accuracy of the detection of the engagement between the engagement recesses 611 of the drive transmission members 61 and the engagement projections 441 of the driven members 44.

Further, in Step S173, after the engagement of the engagement recesses 611 of the drive transmission members 61 with the engagement projections 441 of the driven members 44 is detected by the optical sensor 21c, the drive parts 21b are rotated by the predetermined rotational angle while maintaining the rotational direction. With this, even if there is a misalignment between the target rotational position where the drive transmission members 61 are to be engaged with the driven members 44 and the rotational position of the drive transmission members 61 upon the detection of the completion of the engagement of the driven members 44 with the drive transmission members 61, the misalignment can be eliminated or reduced by the further rotation of the drive parts 21b. As a result, the drive transmission members 61 and the driven members 44 can be more reliably engaged with each other.

In other words, in Step S172, the engagement of the driven members 44 with the drive transmission members 61 is detected by the optical sensor 21c. Then in Step S173, after the engagement of the driven members 44 with the drive transmission members 61 is detected by the optical sensor 21c, the drive parts 21b are further rotated by the predetermined rotational angle while maintaining the rotational direction thereof. With these steps, even if there is a misalignment between the target rotational position where the drive transmission members 61 are to be engaged with the driven members 44 and the rotational position of the drive transmission members 61 upon the detection of the completion of the engagement of the driven members 44 with the drive transmission members 61, the misalignment can be reduced by the further rotation of the drive parts 21b. Therefore, the drive transmission members 61 and the driven members 44 can be more reliably engaged with each other.

The method of fixing the surgical instrument 4 to the robot arm 21 includes Step S18 to notify that the completion of fixing of the surgical instrument 4 to the adaptor 6a. That is, in Step S18, the lamp 21d notifies the worker of the completion of fixing of the surgical instrument 4 to the adaptor 6a.

As described above, in Step S14, based on the detection of the engagement of the engagement projections 211 of the drive parts 21b with the engagement recesses 612 of the drive transmission members 61, the fixing of the adaptor 6a to the robot arm 21 is notified. Accordingly, this allows the worker to check the engagement between the engagement projections 211 of the drive parts 21b and the engagement recesses 612 of the drive transmission members 61. Therefore, the engagement between the engagement projections 211 of the drive parts 21b and the engagement recesses 612 of the drive transmission members 61 can be reliably performed.

In Step S18, based on the detection of the engagement of the engagement recesses 611 of the drive transmission members 61 with the engagement projections 441 of the driven members 44 of the surgical instrument 4, the fixing of the surgical instrument 4 to the adaptor 6a is notified. Accordingly, after the worker checks the engagement between the engagement projections 441 of the driven members 44 and the engagement recesses 611 of the drive transmission members 61, the surgical instrument 4 can be used for the surgery. That is, the surgical instrument 4 in the appropriated engagement state can be used for the surgery.

As described above, in Step S3 (see FIG. 15) in the method of assembling the stopper-attached adaptor, the engagement recesses 611 of the drive transmission members 61 (first engagement portions of drive transmission members) of the adaptor 6a, which is to be engaged with the engagement projections 441 of the driven members 44, are set at the second initial angle $\theta_2$ about the rotational axis G, wherein the second initial angle $\theta_2$ does not correspond to the first initial angle $\theta_1$ at which the engagement projections 441 of the driven members 44 (engagement portions of driven members) are set. That is, the second initial angle $\theta_2$ is different from the first initial angle $\theta_1$. Then, in Step S16 in the method of fixing the surgical instrument 4 to the robot arm 21, the surgical instrument 4 is attached to the drive parts 21b via the adaptor 6a. In Step S17 in the method of fixing the surgical instrument 4 to the robot arm 21, the drive parts 21b are driven to rotate the engagement recesses 611 of the drive transmission members 61 from the second initial angle $\theta_2$ to the first initial angle $\theta_1$, to thereby engage the engagement recesses 611 of the drive transmission members 61 with the engagement projections 441 of the driven members 44. That is, at the start of the operation of engaging the engagement recesses 611 of the drive transmission members 61 with the engagement projections 441 of the driven members 44, the engagement recesses 611 of the drive transmission members 61 of the adaptor 6a are set at the second initial angle $\theta_2$, which does not correspond to the first initial angle $\theta_1$ of the engagement projections 441 of the driven members 44. Accordingly, the initial positions of the engagement recesses 611 of the drive transmission members 61 and the initial positions of the engagement projections 441 of the driven members 44 are not arranged to be too close to each other, so that the engagement recesses 611 are not unintentionally engaged with the engagement projections 441 in an incomplete engagement manner. This can prevent the detection of the completion of the engagement between the engagement projections 441 of the driven members 44 and the engagement recesses 611 of the drive transmission members 61 in the state where the engagement projections 441 of the driven members 44 are incompletely engaged with the engagement recesses 611 of the drive transmission members 61, and can ensure a sufficient rotation angle for rotating the drive transmission members 61. Therefore, the surgical instrument 4 and the adaptor 6a can be engaged with each other in a secure and substantially complete state.

Note that every time the surgical instrument 4 is replaced, the operation of fixing the surgical instrument 4 to the robot arm 21 is executed. Every time the surgical instrument 4 is replaced, the used stopper-attached adaptor 6 may be discarded and a new stopper-attached adaptor 6 may be used. Also, every time the surgical instrument 4 is replaced, the adaptor 6a of the used stopper-attached adaptor 6 may be discarded and the stopper 6b of the used stopper-attached adaptor 6 may be reused and attached to a new adaptor 6a.

Second Embodiment

With reference to FIGS. 18 and 21 to 25, a robotic surgical system 200 according to a second embodiment is described below. In addition to detecting the engagement of the drive transmission members 61 to the driven members 44 in the robotic surgical system 100 according to a first embodiment, the robotic surgical system 200 according to a second embodiment reverses the rotational direction of the drive parts 21b, when the engagement of the drive transmission members 61 to the driven members 44 is not detected. In the drawings, the constituents same as in a first embodiment are designated by the same reference numerals.
(Configuration of Robot Surgical System)

Figure 23:
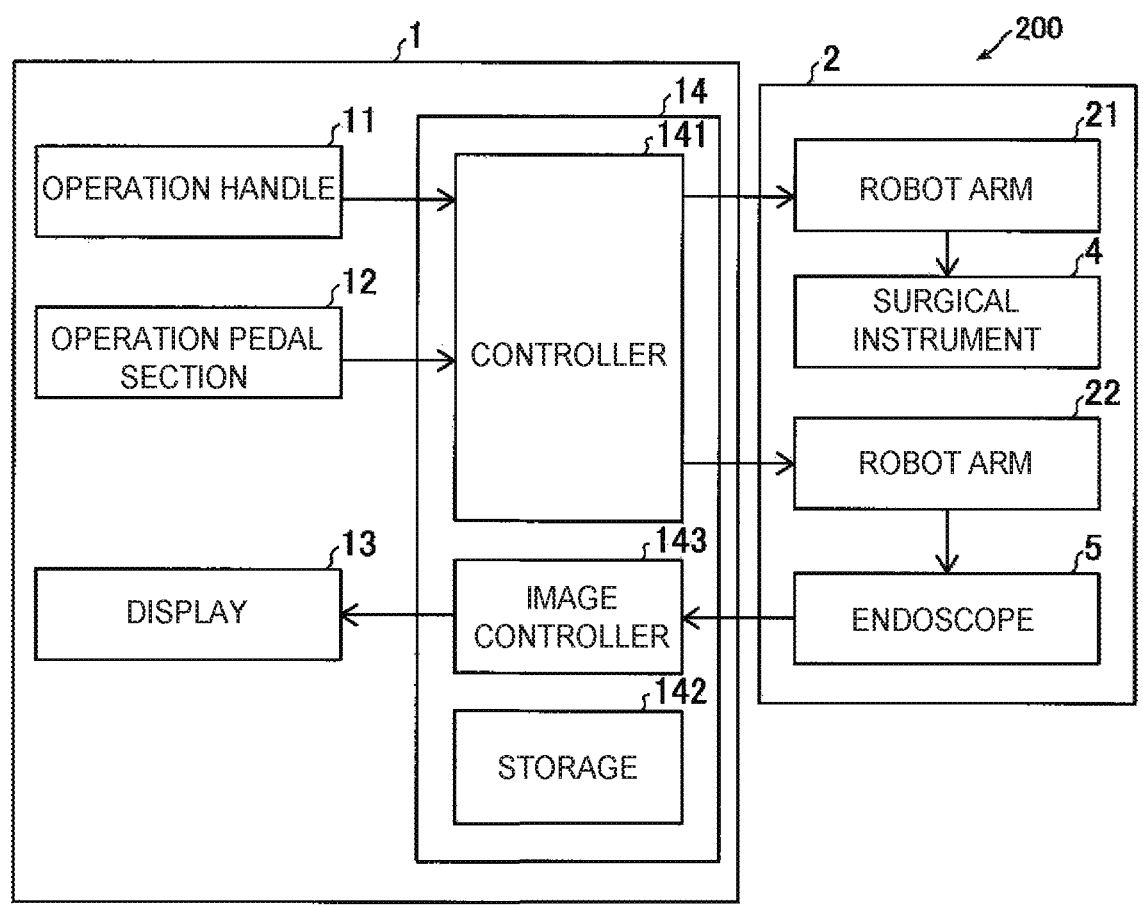
FIG. 23 is a block diagram illustrating a view of a control-related configuration of a robot surgery system according to a second embodiment.
Figure 24:
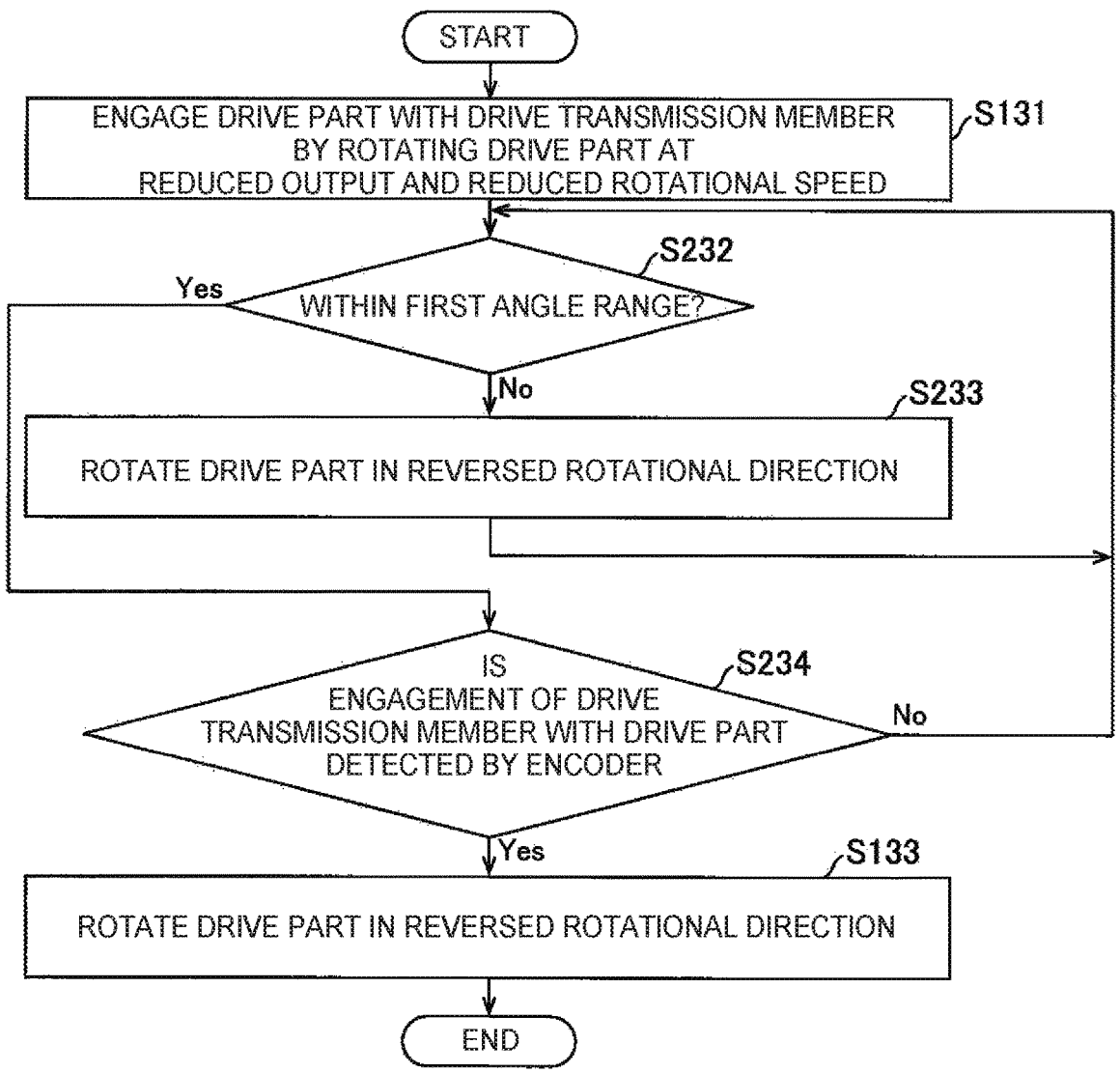
FIG. 24 is a flowchart illustrating a method of engaging drive parts with drive transmission members according to a second embodiment.
Figure 25:
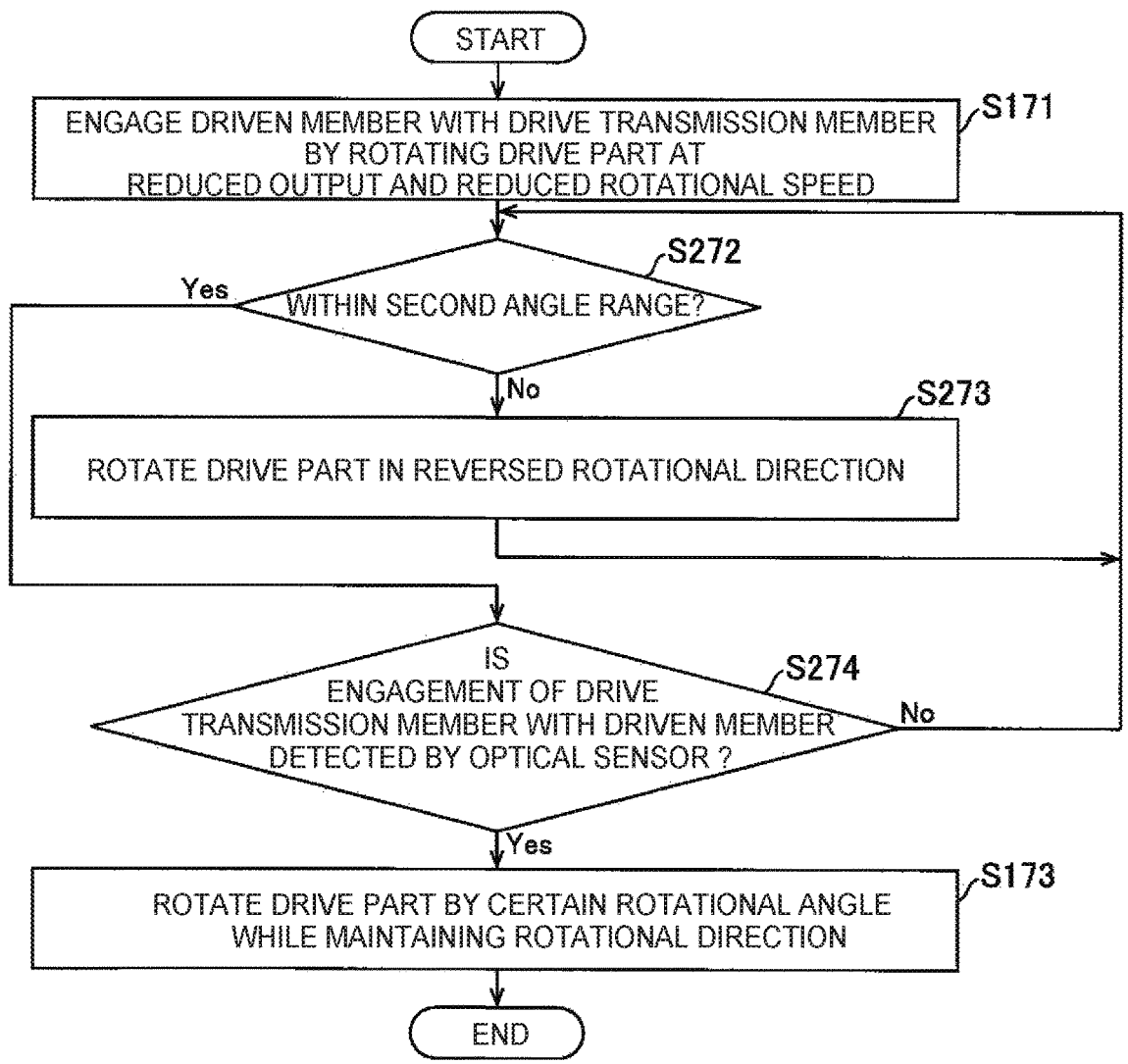
FIG. 25 is a flowchart illustrating a method of engaging the drive transmission members with driven members according to a second embodiment.

With reference to FIG. 23 to FIG. 25, the configuration of the robotic surgical system 200 is described below.

As illustrated in FIG. 23, the robotic surgical system 200 according to a second embodiment includes the remote control apparatus 1 and the patient-side apparatus 2. The remote control apparatus 1 includes the operation handles 11, the operation pedal section 12, the display part 13, and the control apparatus 14. The patient-side apparatus 2 includes the surgical instruments 4, the endoscope 5, the robot arms 21, and the robot arm 22.
(Method of Fixing Surgical Instrument to Robot Arm)

With reference to FIGS. 18 and 21 to 25, a method of fixing the surgical instrument 4 to the robot arm 21 is described below. Note that descriptions of steps in the method of fixing the surgical instrument 4 to the robot arm 21 same as a first embodiment are omitted below to avoid redundancy.

The method of fixing the surgical instrument 4 to the robot arm 21 according to a second embodiment includes Step 13 to engage the engagement projections 211 of the drive parts 21b to the engagement recesses 612 of the drive transmission members 61 set at the third initial angle $\theta_3$. Step S13, which is the method of engaging the drive parts 21b and the drive transmission members 61 with each other, includes Step 131 to engage the engagement projections 211 of the drive parts 21b with the engagement recesses 612 of the drive transmission members 61 by driving the drive parts 21b with the reduced output and the reduced rotational speed of the drive parts 21b.

Step S13 to engage the engagement projections 211 of the drive parts 21b to the engagement recesses 612 of the drive transmission members 61 includes Step S233. In Step S233, when the engagement of the engagement projections 211 of the drive parts 21b with the engagement recesses 612 is not detected within a first predetermined angle range, the rotational direction of the drive parts 21b is reversed. That is, in Step S233, until the engagement of the engagement projections 211 of the drive parts 21b to the engagement recesses 612 is detected within the first predetermined angle range, the rotational direction of the drive parts 21b is repeatedly switched.

Accordingly, when the engagement of the engagement projections 211 of the drive parts 21b with the engagement recesses 612 is not detected within the first predetermined angle range, the rotational direction of the drive parts 21b can be reversed immediately after out of the first predetermined angle range, unlike a case where the drive parts 21b keep rotating in the same direction until the engagement of the engagement projections 211 of the drive parts 21b to the engagement recesses 612 is detected. As a result, the time required to detect the engagement between the engagement recesses 612 and the engagement projections 211 of the drive parts 21b can be shortened.

Specifically, in Step S232, when the engagement projections 211 of the drive parts 21b are rotated from the fourth initial angle 64 toward the engagement recesses 612 of the drive transmission members 61 set at the third initial angle 63, it is determined whether or not the rotational angle of the engagement projections 211 of the drive parts 21b detected by the encoder 215 is within the first predetermined angle range. When it is determined that the rotational angle of the engagement projections 211 of the drive parts 21b is within the first predetermined angle range, the process proceeds to Step S234. To the contrary, when it is determined that the rotational angle of the engagement projections 211 of the drive parts 21b is out of the first predetermined angle range, the process proceeds to Step S233. In Step S233, the rotational direction of the drive parts 21b is reversed and then the process returns to Step S232. That is, when it is determined that the rotational angle of the engagement projections 211 of the drive parts 21b is out of the first predetermined angle range, the rotational direction of the engagement projections 211 of the drive parts 21b is switched to the direction opposite to the rotational direction in which the drive parts 21b was rotated immediately before.

Here, the first predetermined angle range is an angle range within which it is assumed that the engagement projections 211 of the drive parts 21b rotated from the fourth initial angle $\theta_4$ are to be engaged with the engagement recesses 612 of the drive transmission members 61 set at the third initial angle $\theta_3$. The first predetermined angle range is defined as a range having the third initial angle $\theta_3$ being the center of the range with a positive angle toward the second circumferential direction R2 and with a negative angle toward the first circumferential direction R1 from the third initial angle $\theta_3$. The first predetermined angle range is set to an angle range between the third initial angle $\theta_3\pm\alpha$. In a second embodiment, $\alpha$ is set to 20 degrees. Note that $\alpha$ can be more than 0 degree and less than 180 degrees. It may be preferable that $\alpha$ is set to not less than 5 degrees and not more than 25 degrees.

In Step S234, it is determined whether or not the engagement of the engagement projections 211 of the drive parts 21b with the engagement recesses 612 of the drive transmission members 61 is detected by the encoder 215. When it is determined that the engagement is detected by the encoder 215, the process proceeds to Step S133. When it is determined that the engagement is not detected by the encoder 215, the process returns to Step S232.

After executing Step S133, the method of engaging the drive parts 21b and the drive transmission members 61 is ended. As described above, in Step S133, after the engagement of the engagement projections 211 of the drive parts 21b with the engagement recesses 612 of the drive transmission members 61 is detected, the drive parts 21b are rotated in the reversed rotational direction opposite to the rotational direction of the drive parts 21b before the detection of the engagement.

The method of fixing the surgical instrument 4 to the robot arm 21 further includes Step S17 to engage the drive transmission members 61 to the driven members 44 set at the first initial angle $\theta_1$. Step S17 includes Step S171 to drive the drive parts 21b with the reduced output (torque) and the reduced rotational speed, to thereby engage the drive transmission members 61 with the driven members 44.

Step S17 to engage the engagement recesses 611 of the drive transmission members 61 with the engagement projections 441 of the driven members 44 further includes Step S273 to reverse the rotational direction of the drive transmission members 61, when the engagement between the engagement projections 441 of the driven members 44 and the engagement recesses 611 of the drive transmission members 61 is not detected within a second predetermined angle range. That is, in Step S273, until the engagement of the engagement recesses 611 of the drive transmission members 61 with the engagement projections 441 of the driven members 44 is detected within the second predetermined angle range, the rotational direction of the drive parts 21b is repeatedly switched.

Accordingly, when the engagement of the engagement recesses 611 of the drive transmission members 61 to the engagement projections 441 of the driven members 44 is not detected within the second predetermined angle range, the rotational direction of the drive parts 21b can be reversed immediately after out of the second predetermined angle range, unlike a case where the drive parts 21b keep rotating in the same direction until the engagement is detected. As a result, the time required to detect the engagement between the engagement recesses 611 of the drive transmission members 61 and the engagement projections 441 of the driven members 44 can be shortened.

Specifically, in Step S272, when the engagement recesses 611 of the drive transmission members 61 are rotated from the second initial angle $\theta_2$ toward the engagement projections 441 of the driven members 44 set at the first initial angle $\theta_1$, it is determined whether the rotational angle of the engagement projections 211 of the drive parts 21b detected by the encoder 215 is within the second predetermined angle range. When it is determined that the rotational angle of the engagement projections 211 of the drive parts 21b is within the second predetermined angle range, the process proceeds to Step S274. To the contrary, when it is determined that the rotational angle of the engagement projections 211 of the drive parts 21b is out of the second predetermined angle range, the process proceeds to Step S273. In Step S273, the rotational direction of the drive parts 21b is reversed and then the process returns to Step S272. That is, when it is determined that the rotational angle of the engagement projections 211 of the drive parts 21b is out of the second predetermined angle range, the rotational direction of the engagement projections 211 of the drive parts 21b is switched to the direction opposite to the rotational direction in which the drive parts 21b was rotated immediately before.

Here, the second predetermined angle range is an angle range within which it is assumed that the engagement recesses 611 of the drive transmission members 61 rotated from the second initial angle $\theta_2$ are to be engaged with the engagement projections 441 of the driven members 44 set at the first initial angle $\theta_1$. The second predetermined angle range is defined as a range having the first initial angle $\theta_1$ being the center of the range with a positive angle toward the second circumferential direction R2 and with a negative angle toward the first circumferential direction R1 from the first initial angle $\theta_1$. In a second embodiment, the second predetermined angle range is set to an angle range between the first initial angle $\theta_1\pm\beta$. In a second embodiment, $\beta$ is set to 20 degrees. Note that $\beta$ can be more than 0 degree and less than 180 degrees. It may be preferable that $\beta$ is set to not less than 5 degrees and not more than 25 degrees. Note that in a case where the second initial angle $\theta_2$ of the engagement recesses 611 of the drive transmission members 61 is different from the third initial angle $\theta_3$ of the engagement recesses 612 of the drive transmission members 61, the second predetermined angle range is different from the above described value. For example, if the engagement recesses 611 of the drive transmission members 61 is inclined with respect to the engagement recesses 612 of the drive transmission members 61 to the first circumferential direction R1 by $\gamma$ degrees, the second initial angle $\theta_2$ is equal to a value of $\theta_3-\gamma$, and thus the second predetermined angle range is a value of $\theta_1\pm\beta+\gamma$. If the engagement recesses 611 of the drive transmission members 61 is inclined with respect to the engagement recesses 612 of the drive transmission members 61 in the second circumferential direction R2 by $\gamma$ degrees, the second initial angle $\theta_2$ is equal to a value of $\theta_3+\gamma$, and thus the second predetermined angle range is a value of $\theta_1\pm\beta-\gamma$.

In Step S274, it is determined whether the engagement of the engagement recesses 611 of the drive transmission members 61 with the engagement projections 441 of the driven members 44 is detected by the optical sensor 21c. When it is determined that the engagement is detected by the optical sensor 21c, the process proceeds to Step S173. To the contrary, it is determined that the engagement is not detected by the optical sensor 21c, the process returns to Step S272.

After executing Step S173, the method of engaging the drive transmission members 61 with the driven members 44 is ended. As described above, in Step S173, when the controller 141 determines, based on the detection result of the optical sensor 21c, that the driven members 44 are engaged with the drive transmission members 61 by the rotation of the drive parts 21b, the controller 141 overruns the drive parts 21b by the predetermined rotational angle. Note that other configurations and effects of a second embodiment are same as or similar to those of a first embodiment.

Third Embodiment

Next, with reference to FIGS. 15, 18 and 24 to 30, a robotic surgical system 300 according to a third embodiment is described. The robotic surgical system 300 according to a third embodiment is different from the robotic surgical systems 100 and 200 according to first and second embodiments, in that the robotic surgical systems 100 and 200 according to first and second embodiments include the plural fitting projections 665 provided at the stopper body 64 are line-symmetrically arranged with respect to the center axis C2 of the stopper body 64 parallel to the longitudinal direction of the surgical instrument 4 so as to be inclined with respect to the center axis C2 by the predetermined angle θ, whereas the robotic surgical system 300 according to a third embodiment includes plural fitting projections 865 provided at a stopper body 864 are inclined at a predetermined angle θ toward the same direction with respect to a center axis C2 of the stopper body 864 parallel to the longitudinal direction of the surgical instrument 4. Note that in the drawings, the constituents same as in a first embodiment or a second embodiment are designated by the same reference numerals.

(Configuration of Robot Surgical System)

With reference to FIGS. 15, 18 and 24 to 30, the configuration of the robotic surgical system 300 is described below.

Figure 26:
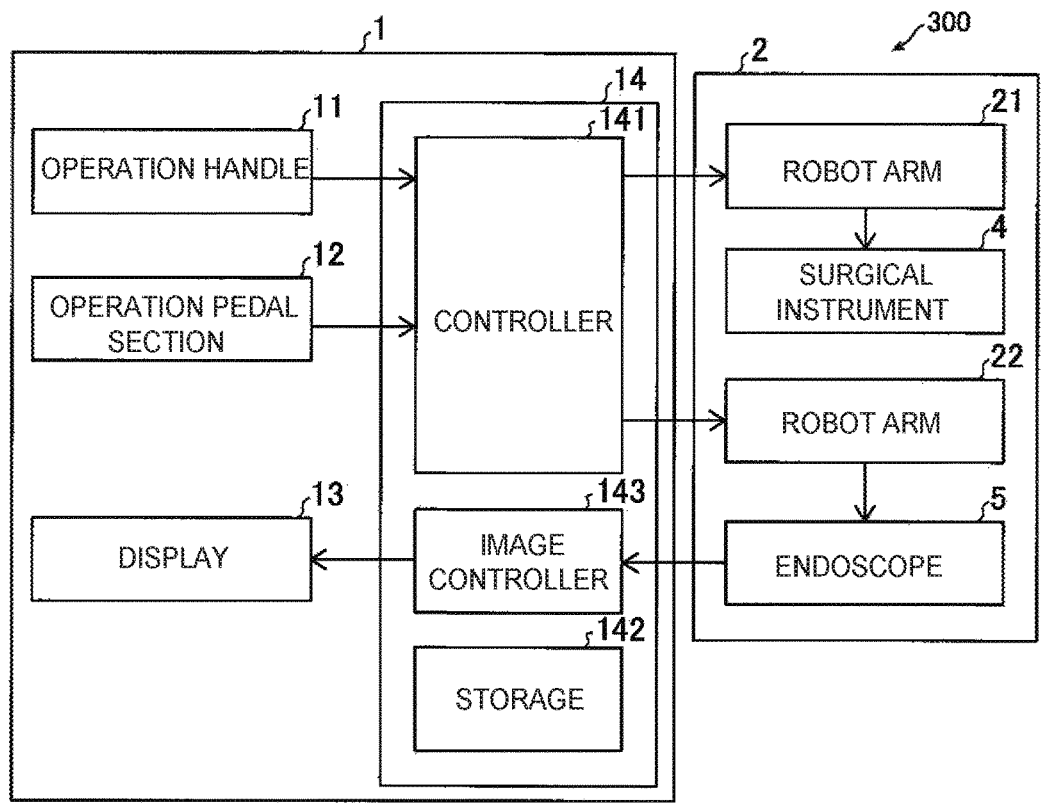
FIG. 26 is a block diagram illustrating a view of a control-related configuration of a robot surgery system according to a third embodiment.

As illustrated in FIG. 26, the robotic surgical system 300 according to a third embodiment includes the remote control apparatus 1 and the patient-side apparatus 2. The remote control apparatus 1 includes the operation handles 11, the operation pedal section 12, the display part 13, and the control apparatus 14. The patient-side apparatus 2 includes the surgical instruments 4, the endoscope 5, the robot arms 21, and the robot arm 22.

(Method of Assembling Stopper-Attached Adaptor)

Figure 27:
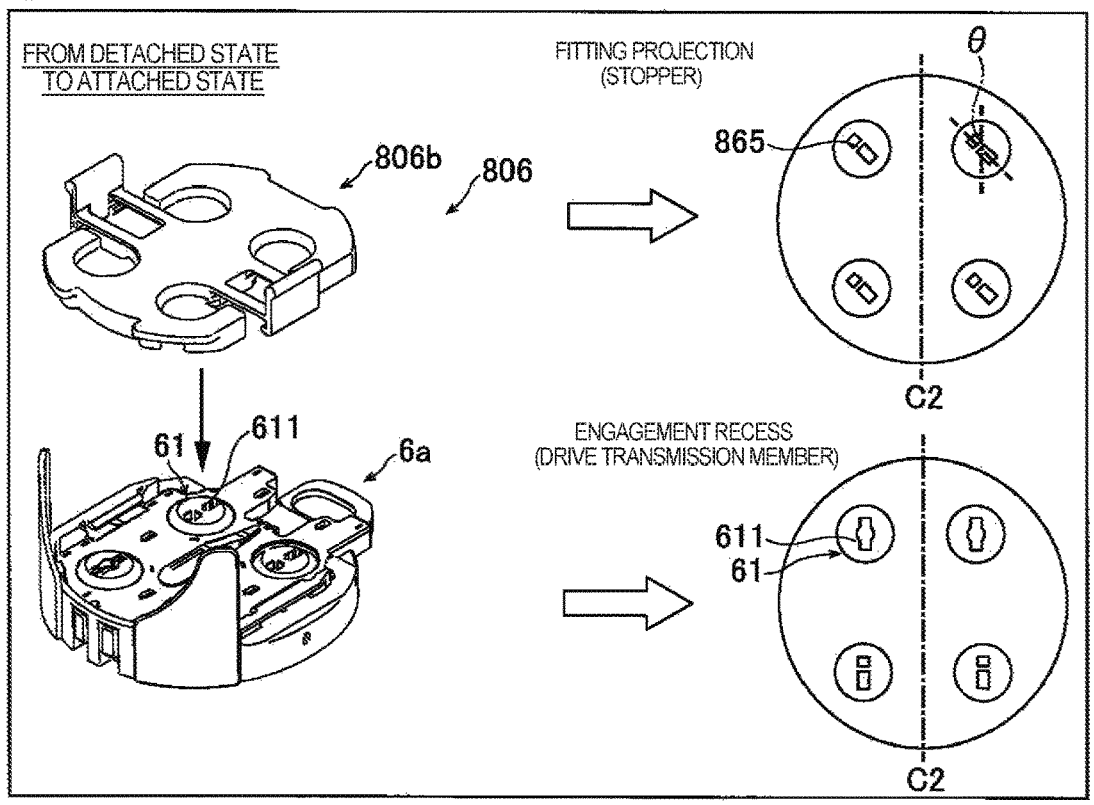
FIG. 27 is a diagram illustrating a schematic view of a state when a stopper is attached to drive transmission members according to a third embodiment.
Figure 28:
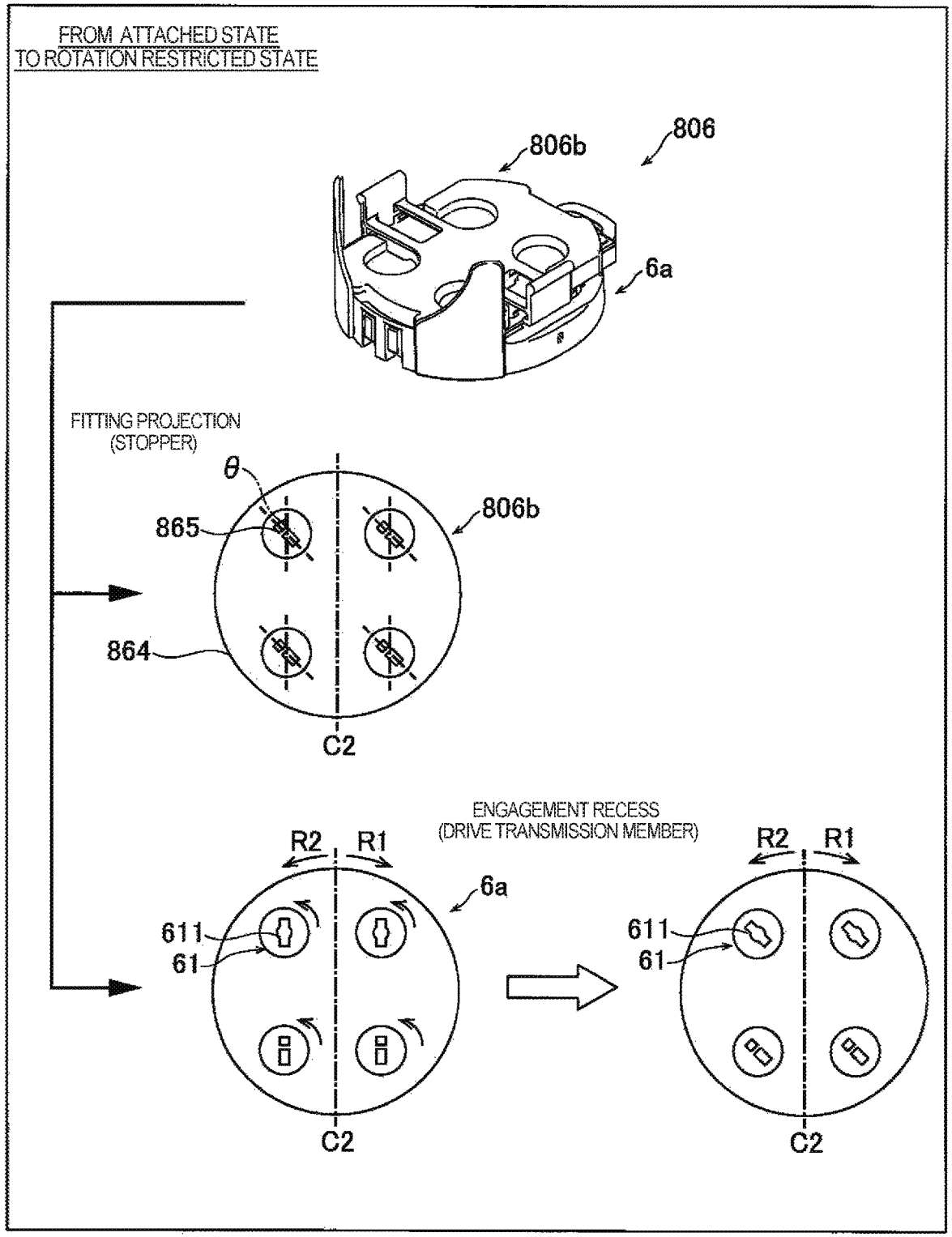
FIG. 28 is a diagram illustrating a schematic view of a state in which rotations of the drive transmission members are restricted by the stopper according to a third embodiment.

Hereinafter, with reference to FIGS. 15, 27, and 28, a method of assembling a stopper-attached adaptor 806, which includes the adaptor 6a and a stopper 806b, is described. By this assembling method, the stopper-attached adaptor 806 is set up which is capable of retaining a state in which the inclination angle of the engagement recesses 611 of the adaptor 6a is fixed at the predetermined angle θ. Note that in FIGS. 27 and 28, the center axis C2 is illustrated to the adaptor 6a and the first circumferential direction R1 and the second circumferential direction R2 are illustrated to the adaptor 6a, to facilitate understanding.

As illustrated in FIG. 15, in Step S1, the worker assembles the adaptor 6a.

In Step S2, the worker attaches the stopper 806b to the adaptor 6a. Specifically, as illustrated in FIG. 27, the worker puts the detached stopper 806b closer to the adaptor 6a, and then attaches the stopper 806b to the adaptor 6a in a state where the fitting projections 865 of the stopper 806b and the drive transmission members 61 of the adaptor 6a are in contact with each other. In this state, the fitting projections 865 of the stopper 806b are inclined with respect to the center axis C2 by the predetermined angle θ toward the second circumferential direction R2, while the engagement recesses 611 of the adaptor 6a are substantially parallel to the center axis C2. All of the plural fitting projections 865 of the stopper 806b are inclined with respect to the center axis C2 by the same predetermined angle θ toward the same direction.

As illustrated in FIG. 15, in Step S3, the worker rotates the drive transmission members 61 of the adaptor 6a to thereby fit the engagement recesses 611 of the adaptor 6a and the fitting projections 865 of the stopper 806b to each other. Specifically, as illustrated in FIG. 27, the worker rotates the drive transmission members 61 of the adaptor 6a manually (for example, operating directly by hand or using a tool) in the state where the stopper 806b is attached to the adaptor 6a, to thereby fit the engagement recesses 611 of the adaptor 6a and the fitting projections 865 of the stopper 806b to each other. At this time, the worker rotates all the engagement recesses 611 of the adaptor 6a in the second circumferential direction R2.

(Method of Fixing Surgical Instrument to Robot Arm)

With reference to FIGS. 18, 24, 25, 29, and 30, a method of fixing the surgical instrument 4 to the robot arm 21 is described below. Note that in FIGS. 29 and 30, the center axis C2 and the center axis G are also illustrated to the adaptor 6a, the drive parts 21b, and the surgical instrument 4 to facilitate understanding and the first circumferential direction R1 and the second circumferential direction R2 are also illustrated to the adaptor 6a, the drive parts 21b and the surgical instrument 4 to facilitate understanding.

As illustrated in FIG. 18, in Step S16 in the method of fixing the surgical instrument 4 to the robot arm 21, the surgical instrument 4 is attached to the drive parts 21b via the adaptor 6a in a state where the engagement recesses 611 of the drive transmission members 61 (first engagement portions of drive transmission members) of the adaptor 6a, which are to be engaged with the engagement projections 441 of the driven members 44, are set at the second initial angle $θ_2$, which does not correspond to the first initial angle $θ_1$ about the rotational axis G at which the engagement projections 441 of the driven members 44 (engagement portions of driven members) is set. In Step S17 in the method of fixing the surgical instrument 4 to the robot arm 21, the drive parts 21b are driven to rotate the drive transmission members 61 having the engagement recesses 611 from the second initial angle $θ_2$ in the first circumferential direction R1, to thereby engage the engagement recesses 611 of the drive transmission members 61 to the engagement projections 441 of the driven members 44.

Figure 29:
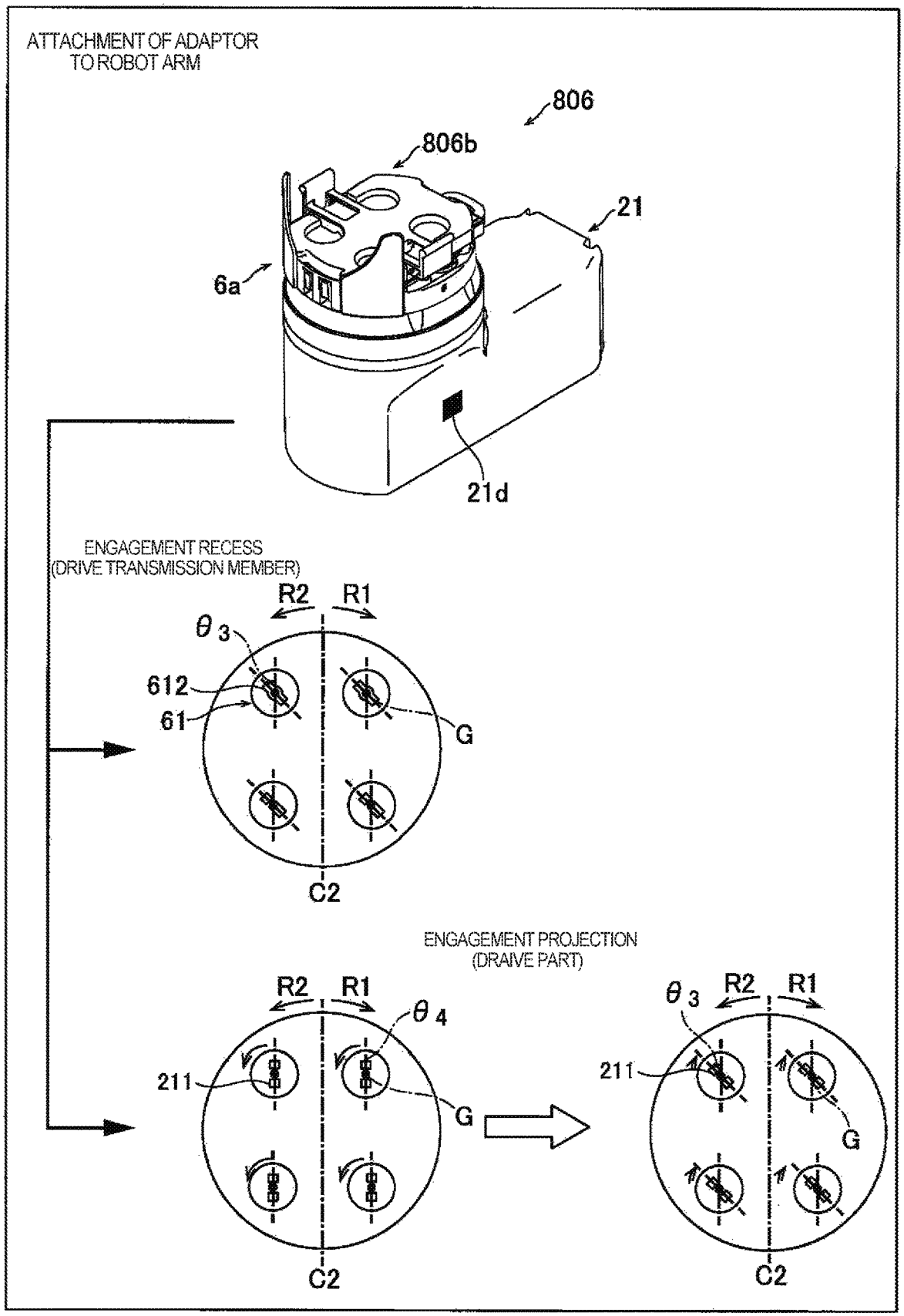
FIG. 29 is a diagram illustrating a schematic view of a state when an adaptor is attached to a robot arm according to a third embodiment.

As illustrated in FIGS. 18 and 29, the method of fixing the surgical instrument 4 to the robot arm 21 includes attaching the adaptor 6a to the robot arm 21, and then rotating the drive parts 21b in the second circumferential direction R2, to thereby engage the engagement projections 211 of the drive parts 21b with the engagement recesses 612 of the drive transmission members 61 set at the third initial angle $θ_3$ (predetermined angle θ).

The method of fixing the surgical instrument 4 to the robot arm 21 includes S12 in which the worker (the assistant Sp (see FIG. 1)) attaches, to the drive parts 21b of the robot arm 21, the drive transmission members 61 whose engagement recesses 611 are set at the second initial angle $θ_2$ and engagement recesses 612 are set at the third initial angle $θ_3$.

The method of fixing the surgical instrument 4 to the robot arm 21 includes Step S13 to engage the engagement projections 211 of the drive parts 21b to the engagement recesses 612 of the drive transmission members 61 set at the third initial angle $θ_3$.

Step S13 to engage the engagement projections 211 of the drive parts 21b to the engagement recesses 612 of the drive transmission members 61 includes Step S233. In Step S233, when the engagement of the engagement projections 211 of the drive parts 21b to the engagement recesses 612 is not detected within the first predetermined angle range, the drive parts 21b are rotated in the reversed direction opposite to the rotational direction in which the drive part 21b was rotated immediately before.

Specifically, in Step S232, when the engagement projections 211 of the drive parts 21b are rotated from the fourth initial angle $θ_4$ toward the engagement recesses 612 of the drive transmission members 61 set at the third initial angle $\theta_3$, it is determined whether or not the rotational angle of the engagement projections 211 of the drive parts 21b detected by the encoder 215 is within the first predetermined angle range. When it is determined that the rotational angle of the engagement projections 211 of the drive parts 21b is within the first predetermined angle range, the process proceeds to Step S234. To the contrary, when it is determined that the rotational angle of the engagement projections 211 of the drive parts 21b is out of the first predetermined angle range, the process proceeds to Step S233. In Step S233, the rotational direction of the drive parts 21b is reversed.

In Step S234, it is determined whether or not the engagement of the engagement projections 211 of the drive parts 21b with the engagement recesses 612 of the drive transmission members 61 is detected by the encoder 215. When it is determined that the engagement is detected by the encoder 215, the process proceeds to Step S133. When it is determined that the engagement is not detected by the encoder 215, the process returns to Step S232.

After executing Step S133, the method of engaging the drive parts 21b and the drive transmission members 61 is ended and the process proceeds to Step S14. As described above, in Step S133, after the engagement of the engagement projections 211 of the drive parts 21b with the engagement recesses 612 of the drive transmission members 61 is detected, the drive parts 21b are rotated in the reversed direction opposite to the rotational direction of the drive parts 21b before the detection of the engagement. Note that Steps S14 to S16 of a third embodiment are the same as those of a first embodiment and thus descriptions thereof are omitted to avoid redundancy.

Figure 30:
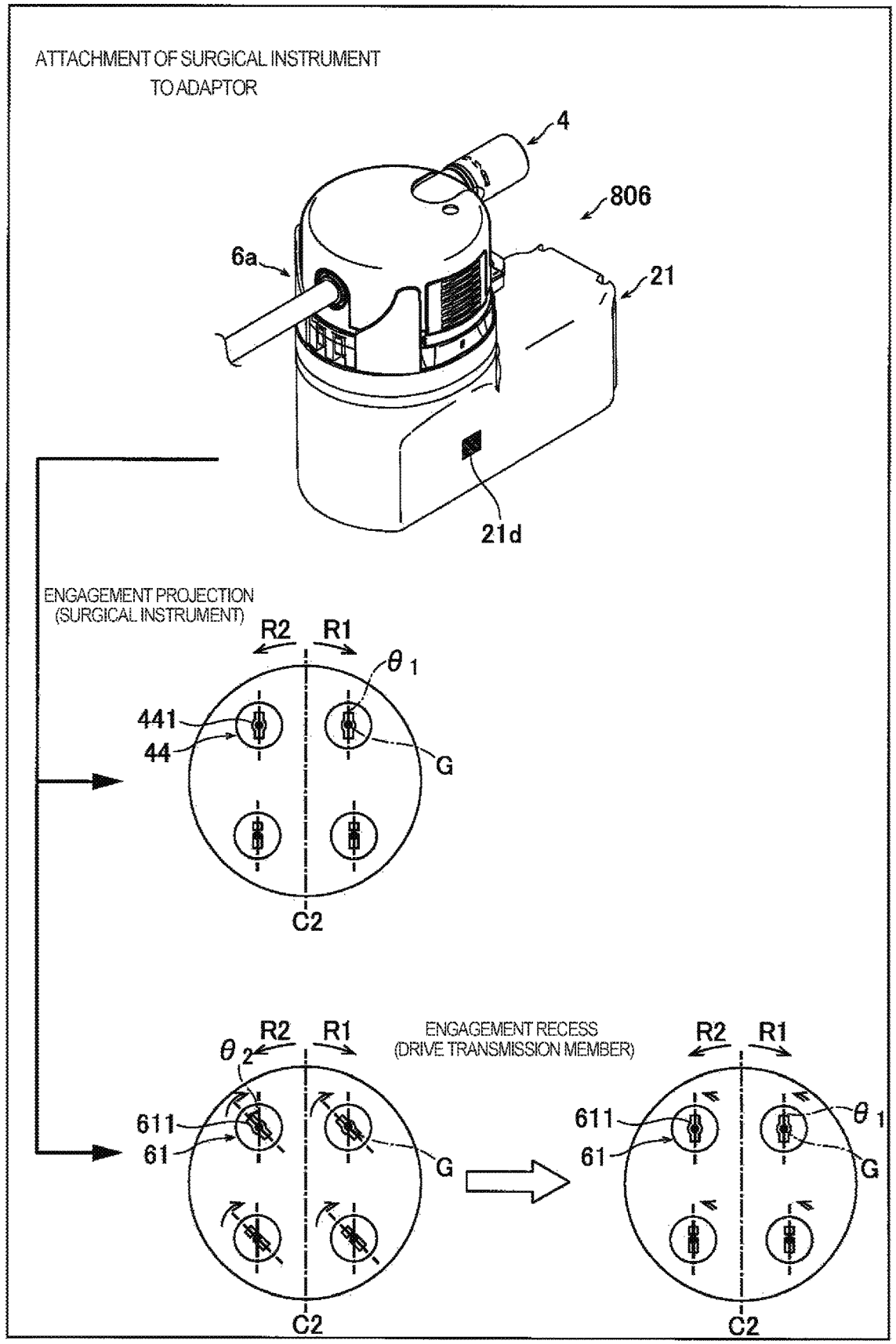
FIG. 30 is a diagram illustrating a schematic view of a state when a surgical instrument is attached to the adaptor according to a third embodiment.
Figure 31:
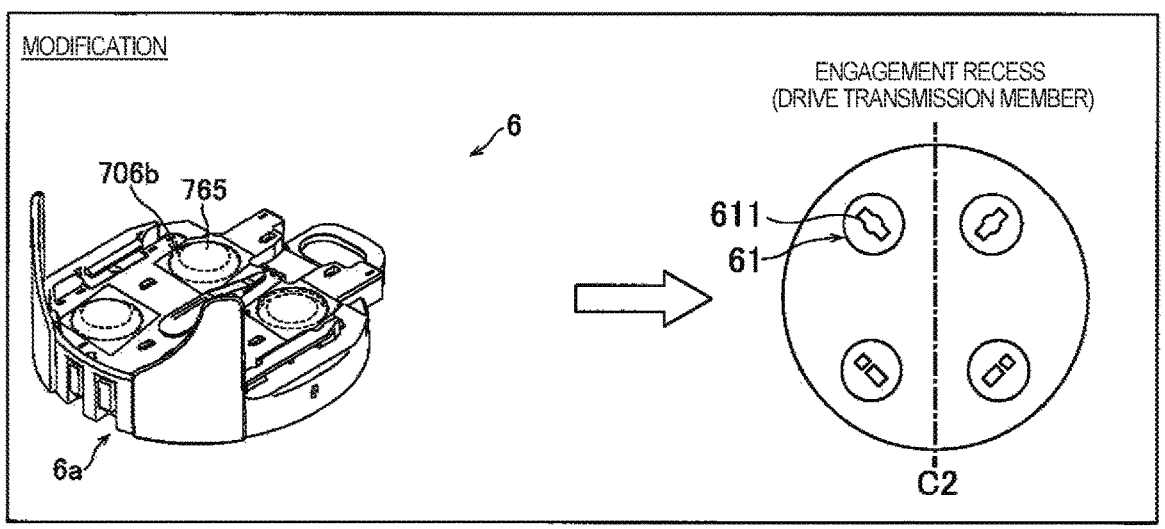
FIG. 31 is a diagram illustrating a schematic view of a stopper according to a modification of first to third embodiments.

As illustrated in FIGS. 18 and 30, the method of fixing the surgical instrument 4 to the robot arm 21 includes Step S17 to engage the drive transmission members 61 to the driven members 44 set at the first initial angle $\theta_1$. Step S17 includes Step S171 to drive the drive parts 21b at the reduced output (torque) and the reduced rotational speed, to thereby engage the drive transmission members 61 to the driven members 44.

Step S17 to engage the engagement recesses 611 of the drive transmission members 61 to the engagement projections 441 of the driven members 44 further includes Step S273 to reverse the rotational direction of the drive transmission members 61, when the engagement between the engagement projections 441 of the driven members 44 and the engagement recesses 611 of the drive transmission members 61 is not detected within the second predetermined angle range.

Specifically, in Step S273, when the engagement recesses 611 of the drive transmission members 61 are rotated from the second initial angle $\theta_2$ toward the engagement projections 441 of the driven members 44 set at the first initial angle $\theta_1$, it is determined whether or not the rotational angle of the engagement projections 211 of the drive parts 21b detected by the encoder 215 is within the second predetermined angle range. When it is determined that the rotational angle of the engagement projections 211 of the drive parts 21b is within the second predetermined angle range, the process proceeds to Step S274. To the contrary, when it is determined that the rotational angle of the engagement projections 211 of the drive parts 21b is out of the second predetermined angle range, the process proceeds to Step S273, to reverse the rotational direction of the drive parts 21b.

In Step S274, it is determined whether or not the engagement of the engagement recesses 611 of the drive transmission members 61 with the engagement projections 441 of the driven members 44 is detected by the optical sensor 21c. When it is determined that the engagement is detected by the optical sensor 21c, the process proceeds to Step S173. To the contrary, when it is determined that the engagement is not detected by the optical sensor 21c, the process returns to Step S272.

After executing Step S173, the method of engaging the drive transmission members 61 to the driven members 44 is ended, and the process proceeds to Step S18. As described above, in Step S173, when the controller 141 determines, based on the detection result of the optical sensor 21c, that the drive transmission members 61 are engaged with the driven members 44 by the rotation of the drive parts 21b, the controller 141 overruns the drive parts 21b by the predetermined rotational angle. Note that other configurations and effects of a third embodiment are same as or similar to those of a first or second embodiment.

(Modifications)

One or more embodiments disclosed above are meant to be illustrative in all respects and should not be construed to be limiting in any manner. The scope of the disclosure is defined not by the above-described one or more embodiments, but by the scope of claims, and includes all modifications (variations) within equivalent meaning and scope to those of the claims.

For example in above described first to third embodiments, the stopper-attached adaptor 6 includes the stopper 6b (806b) to fix the rotational positions of the engagement recesses 611 of the adaptor 6a to the predetermined inclined angle θ. However, the disclosure is not limited to this. For example, in a modification as illustrated in FIG. 23, the stopper 706b may have tapes 765 to fix the rotational positions of the engagement recesses 611 of the adaptor 6a to the predetermined inclined angle θ. In this case, an adhesive layer of the tape 765 forms a rotation restriction portion, and a base of the tape 765 on which the adhesive layer is provided forms a stopper body.

In above described first to third embodiments, the robot arm 21 includes the lamp 21d whose lighting state is changed either when the engagement between the robot arm 21 and the adaptor 6a is completed or when the engagement between the adaptor 6a and the surgical instrument 4 is completed. However, the disclosure is not limited to this. For example, in a modification, a robot arm may include a notification part such as a sound generator to generate sound either when an engagement between the robot arm and an adaptor is completed or when an engagement between the adaptor and a surgical instrument is completed.

In above described first to third embodiments, the attachment portion 664 is configured to attach the stopper body 64 to the adaptor 6a when the stopper body 64 is put closer to the adaptor 6a in the Z direction and to detach the stopper body from the adaptor 6a when the stopper body is put away from the adaptor 6a in the Z direction. However, the disclosure is not limited to this. For example, in a modification, an attachment portion may be configured to attach a stopper body to an adaptor when the stopper body is slid closer to the adaptor in the Y direction and to detach the stopper body from the adaptor when the stopper body is slid away from the adaptor in the Y direction.

In above described first to third embodiments, the plural (four) fitting projections 665 are provided on the surface of the stopper body 64 (864) opposed to the surgical instrument 4 side surface 63 of the adaptor 6a. However, the disclosure is not limited to this. For example, in a modification, the number of fitting projections is set corresponding to the number of drive transmission members, and may be one to three or more than four.

In above described first to third embodiments, the plural fitting projections 665 (865) are arranged on the stopper body 64 (854) to be line-symmetric with respect to the center axis C2 of the stopper body and be inclined at the predetermined angle θ with respect to the center axis C2. However, the disclosure is not limited to this. For example, in a modification, plural fitting projections may be provided at positions corresponding to drive transmission members of an adaptor, but the plural fitting projections are not required to be line-symmetrically arranged with respect to a center axis of a stopper body.

In above described first to third embodiments, the number of the plural fitting projections 665 (865) provided on the X1 side with respect to the center axis C2 of the stopper body 64 (864) and the number of the plural fitting projections 665 (865) provided on the X2 side with respect to the center axis C2 of the stopper body are the same. However, the disclosure is not limited to this. For example, in a modification, the number of plural fitting projections provided on an X1 side with respect to a center axis of a stopper body and the number of plural fitting projections provided on an X2 side with respect to the center axis of the stopper body may be different. Also, plural fitting projections may be provided on only the X1 side or the X2 side with respect to the center axis of the stopper body.

In above described first to third embodiments, the discrimination portion 667 includes the first discrimination portion 667a (discrimination portion) in which one side portion of the stopper body 64 (864) is smaller than the other side portion of the stopper body in the Y direction and the second discrimination portion 667b (discrimination portion) having the recess or the cutout at only one side of the rim of the stopper body. However, the disclosure is not limited to this. For example, in a modification, a discrimination portion may include only one of a first discrimination portion in which one side portion of a stopper body is smaller than the other side portion of the stopper body in a longitudinal direction of a surgical instrument and a second discrimination portion having a recess or a cutout at only one side of an end of the stopper body.

In above described first to third embodiments, the encoder 215 detects the engagement state between the drive parts 21b and the drive transmission members 61. However, the disclosure is not limited to this. For example, in a modification, a controller may detect an engagement state of drive parts and drive transmission members by measuring an electrical current value(s) applied to a motor(s) of the drive part(s).

In above described first to third embodiments, the stopper 6b (806b) is provided with the fitting projections 665 (865), and the adaptor 6a is provided with the engagement recesses 611. However, the disclosure is not limited to this. For example, in a modification, a stopper may be provided with fitting recess(es) and an adaptor may be provided with fitting projection(s).

In above described first to third embodiments, the method of fixing the surgical instrument 4 to the robot arm 21 is the method of fixing the surgical instrument 4 to the drive parts 21b of the robot arm 21 via the adaptor 6a. However, the disclosure is not limited to this. For example, in a modification, a method of fixing a surgical instrument to a robot arm may be a method of fixing the surgical instrument directly to a drive part(s) of the robot arm. In this case, the drive part(s) of the robot arm is attached to a driven member(s) of the surgical instrument in a state where an engagement portion(s) of the drive part(s) of the robot arm is set at a second initial orientation, which is different from a first initial orientation at which an engagement portion(s) of the driven member(s) of the surgical instrument is set, and then the drive part(s) are rotated to thereby engage the drive part(s) of the robot arm with the driven member(s) of the surgical instrument, unlike above described first to third embodiments. If the engagement portion(s) of the drive part(s) of the robot arm is a recess (or a projection) and the engagement portion(s) of the driven member(s) of the surgical instrument is a projection (or a recess), the recessed (or projected) engagement portion(s) of the drive part(s) of the robot arm is to be engaged with the projected (or recessed) engagement portion(s) of the driven member(s) of the surgical instrument. Even in this case, the method of fixing the surgical instrument directly to the robot arm can obtain effects same as or similar to those of the method of fixing the surgical instrument to the robot arm via the adaptor.

In the method of fixing the surgical instrument 4 to the robot arm 21 according to above described first to third embodiments, the rotational angles of the drive transmission members 61 are fixed by the stopper 6b (806b) in advance. However, the disclosure is not limited to this. For example, in a modification, a drive transmission member(s) may be held manually by a worker (assistant) without using a stopper.

In above described first to third embodiments, each of the engagement projections 441 of the driven members 44 includes plural projected portions being linearly arranged. However, the disclosure is not limited to this. For example, in a modification, an engagement projection of a driven member may be formed as a single projection portion or may include plural projected portions being not linearly arranged.

In above described first to third embodiments, each of the engagement recesses 611 and 612 of the drive transmission member 61 is formed as a single recess extending linearly. However, the disclosure is not limited to this. For example, in a modification, an engagement recess of a drive transmission member may include plural recessed portions being linearly arranged or may include plural recessed portions being not linearly arranged.

In above described first to third embodiments, the engagement projection 211 of each of the drive parts 21b includes plural projected portions being linearly arranged, but is not required to include plural projected portions being linearly arranged.

In above described first to third embodiments, the engagement projection 441 of each of the driven members 44 has the line-symmetric shape. However, the disclosure is not limited to this. For example, in a modification, an engagement projection of each driven member may not have a line-symmetric shape.

In above described first to third embodiments, the engagement recess 611 of each of the drive transmission members 61 has the line-symmetric shape but is not required to have a line-symmetric shape.

In above described first to third embodiments, the engagement recess 612 of each of the drive transmission members 61 has the line-symmetric shape but is not required to have a line-symmetric shape.

In above described first to third embodiments, the engagement projection 211 of each of the drive parts 21b has the line-symmetric shape but is not required to have a line-symmetric shape.

In above described first to third embodiments, the engagement recesses 611 of the drive transmission members 61 of the adaptor 6a are manually rotated by the worker of the manufacturer, to thereby fit the engagement recesses 611 of the drive transmission members 61 to the fitting projections 665 (865). However, the disclosure is not limited to this. For example, in a modification, a drive transmission member of a adaptor may be manually rotated by an assistant Sp, to thereby fit an engagement recess of the drive transmission member to a fitting projection.

The invention claimed is:

1. A method of fixing a surgical instrument to a robot arm by fixing a driven member of the surgical instrument to a drive part of the robot arm via an adaptor, wherein the drive part of the robot arm is configured to rotate the driven member of the surgical instrument via a drive transmission member of the adaptor, the method comprising:
    attaching the surgical instrument to the robot arm via the adaptor in a state where a first engagement portion of the drive transmission member of the adaptor, which is to be engaged with an engagement portion of the driven member, is set in a second initial orientation about a rotational axis, wherein the second initial orientation does not correspond to a first initial orientation in which the engagement portion of the driven member is set; and
    engaging the first engagement portion of the drive transmission member with the engagement portion of the driven member, by driving the drive part of the robot arm to rotate the first engagement portion of the drive transmission member from the second initial orientation.

2. The method of fixing the surgical instrument to the robot arm according to claim 1, wherein
    the engaging of the first engagement portion of the drive transmission member with the engagement portion of the driven member comprises:
    engaging the first engagement portion of the drive transmission member with the engagement portion of the driven member, by driving the drive part, with a reduced output of the drive part lower than an output of the drive part when performing a surgery with the surgical instrument, to rotate the first engagement portion of the drive transmission member from the second initial orientation.

3. The method of fixing the surgical instrument to the robot arm according to claim 1, wherein
    the engaging of the first engagement portion of the drive transmission member with the engagement portion of the driven member comprises:
    engaging the first engagement portion of the drive transmission member with the engagement portion of the driven member, by driving the drive part, with a reduced rotational speed of the drive part lower than an rotational speed of the drive part when performing a surgery with the surgical instrument, to rotate the first engagement portion of the drive transmission member.

4. The method of fixing the surgical instrument to the robot arm according to claim 1, wherein
    the engaging of the first engagement portion of the drive transmission member with the engagement portion of the driven member further comprises:
    detecting an engagement of the first engagement portion of the drive transmission member with the engagement portion of the driven member.

5. The method of fixing the surgical instrument to the robot arm according to claim 4, wherein
    the engagement of the first engagement portion of the drive transmission member with the engagement portion of the driven member is detected by an optical sensor.

6. The method of fixing the surgical instrument to the robot arm according to claim 4, wherein
    the engaging of the first engagement portion of the drive transmission member with the engagement portion of the driven member further comprises:
    after detecting the engagement of the first engagement portion of the drive transmission member with the engagement portion of the driven member, further rotating the drive part by a predetermined rotational angle in a rotational direction same as a rotational direction of the drive part before detecting the engagement of the first engagement portion of the drive transmission member with the engagement portion of the driven member.

7. The method of fixing the surgical instrument to the robot arm according to claim 4, further comprising:
    in response to detecting the engagement of the first engagement portion of the drive transmission member with the engagement portion of the driven member, notifying that the surgical instrument is fixed to the adaptor.

8. The method of fixing the surgical instrument to the robot arm according to claim 1, further comprising
    in a state where a second engagement portion of the drive transmission member of the adaptor, which is to be engaged with an engagement portion of the drive part of the robot arm, is set in a third initial orientation, setting the engagement portion of the drive part to a fourth initial orientation, wherein the fourth initial orientation does not correspond to the third initial orientation; and
    after attaching the adaptor to the drive part of the robot arm, rotating the drive part of the robot arm to engage the engagement portion of the drive part with the second engagement portion of the drive transmission member set at the third initial orientation.

9. The method of fixing the surgical instrument to the robot arm according to claim 8, wherein
    the second initial orientation and the third initial orientation are the same orientation.

10. The method of fixing the surgical instrument to the robot arm according to claim 8, wherein
    the engaging of the engagement portion of the drive part with the second engagement portion of the drive transmission member comprises:
    engaging the engagement portion of the drive part with the second engagement portion of the drive transmission member, by rotating the engagement portion of the drive part of the robot arm with a reduced output of the drive part lower than an output of the drive part when performing a surgery with the surgical instrument.

11. The method of fixing the surgical instrument to the robot arm according to claim 8, wherein
    the engaging of the engagement portion of the drive part with the second engagement portion of the drive transmission member comprises:
    engaging the engagement portion of the drive part with the second engagement portion of the drive transmission member, by driving the engagement portion of the drive part of the robot arm with a reduced rotational speed of the drive part lower than a rotational speed of the drive part when performing a surgery with the surgical instrument.

12. The method of fixing the surgical instrument to the robot arm according to claim 8, wherein
the engaging of the engagement portion of the drive part with the second engagement portion of the drive transmission member further comprises:
detecting an engagement of the engagement portion of the drive part with the second engagement portion of the drive transmission member by an encoder; and
rotating, after the engagement of the engagement portion of the drive part with the second engagement portion of the drive transmission member is detected, the drive part in a rotational direction opposite to a rotational direction of the drive part before the engagement of the engagement portion of the drive part with the second engagement portion of the drive transmission member is detected.

13. The method of fixing the surgical instrument to the robot arm according to claim 8, further comprising:
attaching, to the robot arm, the adaptor to which a stopper is attached, wherein the stopper fixes the first engagement portion of the drive transmission member at the second initial orientation;
after engaging the engagement portion of the drive part with the second engagement portion of the drive transmission member, detaching the stopper from the adaptor; and
attaching the surgical instrument to the adaptor after the stopper is detached from the adaptor.

14. The method of fixing the surgical instrument to the robot arm according to claim 8, further comprising:
in response to detecting the engagement of the engagement portion of the drive part with the second engagement portion of the drive transmission member, notifying that the adaptor is fixed to the robot arm.

15. The method of fixing the surgical instrument to the robot arm according to claim 8, wherein
the engaging of the engagement portion of the drive part with the second engagement portion of the drive transmission member comprises:
reversing a rotational direction of the drive part, when the engagement of the engagement portion of the drive part with the second engagement portion of the drive transmission member is not detected in a first predetermined angle range.

16. The method of fixing the surgical instrument to the robot arm according to claim 1, wherein
the engaging of the first engagement portion of the drive transmission member with the engagement portion of the driven member comprises:
reversing a rotational direction of the drive part, when the engagement of the first engagement portion of the drive transmission member with the engagement portion of the driven member is not detected in a second predetermined angle range.

17. The method of fixing the surgical instrument to the robot arm according to claim 1, wherein
the drive part comprises a plurality of drive parts, each of which includes the engagement portion of the drive part,
the drive transmission member comprises a plurality of drive transmission members, each of which includes the first engagement portion of the drive transmission member, and
the driven member comprises a plurality of driven members, each of which includes the engagement portion of the driven member, wherein
the engaging of the first engagement portion of the drive transmission member with the engagement portion of the driven member comprises:
engaging the first engagement portions of the plurality of drive transmission members with the engagement portions of the plurality of driven members, by driving the plurality of drive parts to rotate the first engagement portion of at least one of the plurality of drive transmission members in a first circumferential direction and rotate the first engagement portion of another of the plurality of drive transmission members in a second circumferential direction.

18. The method of fixing the surgical instrument to the robot arm according to claim 1, wherein
the drive part comprises a plurality of drive parts, each of which includes the engagement portion of the drive part,
the drive transmission member comprises a plurality of drive transmission members, each of which includes the first engagement portion of the drive transmission member, and
the driven member comprises a plurality of driven members, each of which includes the engagement portion of the driven member, wherein
the engaging the first engagement portion of the drive transmission member with the engagement portion of the driven member comprises:
engaging the first engagement portions of the plurality of drive transmission members with the engagement portions of the plurality of driven members, by driving the plurality of drive parts to rotate the first engagement portions of the plurality of drive transmission members in the same circumferential direction.

19. A method of fixing a surgical instrument to a robot arm by fixing a driven member of the surgical instrument to a drive part of the robot arm, wherein the drive part of the robot arm is configured to rotate the driven member of the surgical instrument, the method comprising:
attaching the surgical instrument to the drive part of the robot arm in a state where an engagement portion of the drive part, which is to be engaged with an engagement portion of the driven member, is set in a second initial orientation about a rotational axis, wherein the second initial orientation does not correspond to a first initial orientation in which the engagement portion of the driven member is set; and
engaging the engagement portion of the drive part with the engagement portion of the driven member, by driving the drive part of the robot arm to rotate the engagement portion of the drive part from the second initial orientation.

20. A method of fixing a surgical instrument to a robot arm by fixing a driven member of the surgical instrument to a drive part of the robot arm via an adaptor, wherein the drive part of the robot arm is configured to rotate the driven member of the surgical instrument via an drive transmission member of the adaptor, the method comprising:
setting an engagement portion of the drive transmission member of the adaptor, which is to be engaged with an engagement portion of the driven member, to a second initial orientation about a rotational axis, wherein the second initial orientation does not correspond to a first initial orientation in which the engagement portion of the driven member is set;

attaching the surgical instrument to the drive part of the robot arm via the adaptor, after the engagement portion of the drive transmission member is set to the second initial orientation; and engaging the engagement portion of the drive transmission member with the engagement portion of the driven member, by driving the drive part of the robot arm to rotate the engagement portion of the drive transmission member from the second initial orientation, after the surgical instrument is attached to the drive part of the robot arm via the adaptor.

* * * * *